US011951320B2

(12) United States Patent
Marshall et al.

(10) Patent No.: US 11,951,320 B2
(45) Date of Patent: *Apr. 9, 2024

(54) ELECTRODE ARRANGEMENT FOR A CURVILINEAR MEDICAL DEVICE LEAD

(71) Applicant: Medtronic, Inc., Minneapolis, MN (US)

(72) Inventors: Mark T. Marshall, Cape Coral, FL (US); Timothy A. Ebeling, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/061,870

(22) Filed: Dec. 5, 2022

(65) Prior Publication Data

US 2023/0098932 A1   Mar. 30, 2023

Related U.S. Application Data

(63) Continuation of application No. 16/525,908, filed on Jul. 30, 2019, now Pat. No. 11,517,756.

(51) Int. Cl.
*A61N 1/39* (2006.01)
*A61B 5/287* (2021.01)
(Continued)

(52) U.S. Cl.
CPC .......... *A61N 1/39622* (2017.08); *A61B 5/287* (2021.01); *A61N 1/0565* (2013.01); *A61N 1/3621* (2013.01); *A61N 1/3918* (2013.01)

(58) Field of Classification Search
CPC .............. A61N 1/39622; A61N 1/0565; A61N 1/3621; A61N 1/3918; A61B 5/287
See application file for complete search history.

(56) References Cited

U.S. PATENT DOCUMENTS 4,947,866 A   8/1990   Lessar et al.
5,336,253 A   8/1994   Gordon et al.
(Continued)

FOREIGN PATENT DOCUMENTS

EP     3383491 A1    10/2018

OTHER PUBLICATIONS

PCT International Search Report dated Oct. 9, 2020, corresponding to counterpart C00014549WO01, PCT Patent Application No. PCT/US2020/040610; 3 pages.
(Continued)

*Primary Examiner* — Rex R Holmes
*Assistant Examiner* — Jennifer L Ghand
(74) *Attorney, Agent, or Firm* — Shumaker & Sieffert, P.A.

(57) ABSTRACT

A medical electrical lead includes a lead body, a high voltage electrode positioned on the lead body, the high voltage electrode comprising a proximal coated portion, a distal coated portion, and an uncoated portion. Additionally, the medical electrical lead includes a first low voltage electrode and a second low voltage electrode distal to the first low voltage electrode, wherein a first line passes through the first low voltage electrode and the second low voltage electrode, wherein a second line passes through the first low voltage electrode and the uncoated portion, the second line forming a first angle with the first line, and wherein a third line passes through the second low voltage electrode and the uncoated portion, the third line forming a second angle with the first line.

20 Claims, 9 Drawing Sheets

(51) Int. Cl.
*A61N 1/05* (2006.01)
*A61N 1/362* (2006.01)

(56) References Cited

U.S. PATENT DOCUMENTS

| | | | |
|---|---|---|---|
| 5,531,782 A | 7/1996 | Kroll et al. | |
| 5,534,022 A | 7/1996 | Hoffmann et al. | |
| 5,654,030 A | 8/1997 | Munshi et al. | |
| 5,683,443 A | 11/1997 | Munshi et al. | |
| 5,849,031 A | 12/1998 | Martinez et al. | |
| 5,883,714 A | 3/1999 | Jann | |
| 6,327,498 B1 | 12/2001 | Kroll | |
| 7,236,828 B2 | 6/2007 | Casavant et al. | |
| 8,017,179 B2 | 9/2011 | Atanasoska et al. | |
| 11,517,756 B2 * | 12/2022 | Marshall | A61N 1/3918 |
| 2006/0020316 A1 | 1/2006 | Martinez et al. | |
| 2007/0250142 A1 | 10/2007 | Francis et al. | |
| 2010/0305675 A1 | 12/2010 | Laske et al. | |
| 2014/0052120 A1 | 2/2014 | Benscoter et al. | |
| 2016/0121106 A1 | 5/2016 | Marshall et al. | |
| 2016/0158567 A1 | 6/2016 | Marshall et al. | |
| 2017/0157399 A1 * | 6/2017 | Anderson | A61N 1/36521 |
| 2017/0312532 A1 * | 11/2017 | Zhang | A61N 1/3987 |
| 2017/0354365 A1 | 12/2017 | Zhou | |
| 2019/0117970 A1 | 4/2019 | Schmidt et al. | |
| 2021/0031048 A1 | 2/2021 | Marshall et al. | |

OTHER PUBLICATIONS

PCT Written Opinion of the International Searching Authority dated Oct. 9, 2020, corresponding to counterpart C00014549WO01, PCT Patent Application No. PCT/US2020/040610; 6 pages.
Prosecution History from U.S. Appl. No. 16/525,908, dated May 26, 2021 through Aug. 12, 2022, 124 pp.

* cited by examiner

ELECTRODE ARRANGEMENT FOR A CURVILINEAR MEDICAL DEVICE LEAD

This application is a continuation of U.S. patent application Ser. No. 16/525,908, filed Jul. 30, 2019, now issued as U.S. Pat. No. 11,517,756, the contents of which are hereby incorporated by reference in their entirety.

TECHNICAL FIELD

The disclosure relates generally to medical device systems and, more particularly, cardiac sensing and therapy delivery by medical device systems.

BACKGROUND

Some types of implantable medical device (IMD) systems, such as cardiac pacemaker or implantable cardioverter defibrillator systems, may be used to provide cardiac sensing and therapy for a patient via one or more electrodes. Some IMDs include an implantable housing that encloses a pulse generator and other electronic components, which may be configured to be implanted subcutaneously in the chest of the patient, as an example. The IMD may be connected to one or more implantable medical electrical leads that include one or more electrodes. The leads may be configured such that the electrodes may, as examples, be implanted within the heart, e.g., transvenous leads, or outside of the heart and vasculature, e.g., extravascular leads. Extravascular leads of such IMD systems may be configured such that the electrodes, e.g., located on a distal portion of the lead, are implanted subcutaneously, substernally, or in other extravascular locations.

SUMMARY

In general, the disclosure is directed to devices, systems, and techniques for using a medical device lead having an arrangement of electrodes that provides a set of electrode vectors for sensing electrical signals and/or providing electrical therapy. When used for sensing cardiac electrogram signals and/or delivering cardiac pacing, for example, the vectors have differing spatial positions and orientations relative to the heart. In some examples, a resting or implant state of at least a portion of the medical device lead may be curvilinear, positioning the electrodes such that at least two of the set of vectors are not parallel. Non-parallel vectors may enable a medical device coupled to the medical device lead to sense cardiac electrogram signals from different perspectives relative to the heart, or deliver electrical therapy from different perspectives relative to the heart.

Electric signals may be sensed with reference to two points. For example, a medical device may measure a difference in voltage between two electrodes, thus establishing a sensing electrode vector between the two electrodes. The ability to sense according to the set of vectors provided by a medical device lead configured according to the techniques of this disclosure may increase the probability that the medical device will be able to detect and process cardiac depolarizations and other features of a cardiac electrogram, e.g., for determining a therapy to deliver to the patient. Similarly, therapy delivered via different electrical therapy vectors may be differently able to capture target tissue, and the ability of a medical device to select from the set of vectors may increase the probability that therapy is effective and/or allow selection of a vector whose therapy captures the tissue with relatively lower energy consumption.

An example medical device lead may include at least one defibrillation electrode. A defibrillation electrode, in some examples, may be disposed along a curvilinear portion of the medical device lead. The defibrillation electrode may include a proximal coated portion, a distal coated portion, and an uncoated portion between the proximal coated portion and the distal coated portion. The coated portions of the defibrillation electrode may be configured to allow conduction of relatively higher voltage signals and prevent conduction of relatively lower voltage signals. As such, in some cases, the proximal and distal coated portions may be configured to conduct defibrillation pulses, prevent transmission of pacing pulses, and prevent sensing of cardiac depolarizations. The uncoated portion of the defibrillation electrode, in some cases, may be configured to conduct defibrillation pulses, conduct pacing pulses, and allow sensing of cardiac depolarizations. In this way, the uncoated portion of the defibrillation electrode may be configured to, in combination with other electrodes, form vectors for detecting cardiac depolarizations and other cardiac electrical activity, and form cardiac pacing vectors.

In some examples, the defibrillation electrode is disposed along a curvilinear portion of the medical device lead, causing the defibrillation electrode to form an arc, where the uncoated portion of the defibrillation electrode is located at a peak of the arc. Additionally, in some cases, a first pace/sense electrode is disposed on the medical device lead proximal to the defibrillation electrode and a second pace/sense electrode is disposed on the medical device lead distal to the defibrillation electrode. As such, in examples where the defibrillation electrode is arc shaped with the uncoated portion located at the peak of the arc, the uncoated portion of the defibrillation electrode is displaced from an axis between the first pace/sense electrode and the second pace-sense electrode. In this way, the first pace/sense electrode, the second pace/sense electrode, and the uncoated portion of the defibrillation electrode may form three possible vectors: a first vector between the first pace/sense electrode and the second pace/sense electrode, a second vector which extends between the first pace/sense electrode and the uncoated portion, and a third vector between the second pace/sense electrode and the uncoated portion.

The techniques of this disclosure may provide one or more advantages. For example, straight or near-straight medical device leads, or leads of any shape where the pace/sense electrode are located on or near a common axis, might only be able to sense cardiac depolarizations according to vectors that are aligned with a single axis. Example leads having a curvilinear shape, in contrast, may be configured with non-coaxial electrodes that are configured to form vectors that form angles with each other. For example, a first line that passes through the first pace/sense electrode and the second pace/sense electrode may form an angle with a second line that passes through the first pace/sense electrode and the uncoated portion of the defibrillation electrode. Propagation of electric signals during cardiac cycles varies from patient to patient. For example, the heart of each patient may be set slightly differently within the chest cavity, causing a direction of electric depolarizations to vary between patients. As such, it may be beneficial to provide the option to sense cardiac depolarizations according to vectors that are angularly displaced relative to one another, in order to increase a probability of accurately capturing and processing cardiac depolarizations in a large number of patients.

Additionally, it may be beneficial to include an uncoated portion of the defibrillation electrode that is placed at an apex of the curvilinear figure of the defibrillation electrode, where the uncoated portion is relatively small compared to a size of the defibrillation electrode. For example, by making the uncoated portion relatively small compared to the size of the defibrillation electrode, the IMD may be able to increase a length of the vectors and increase an angle that the vectors form with each other. Furthermore, use of an uncoated portion of a defibrillation electrode to provide the set cardiac sensing and/or pacing vectors, instead of the addition of dedicated pace/sense electrodes, may allow a defibrillation electrode and an electrode for pacing and sensing to share a desired position along the medical lead relative to the heart, and may avoid the addition of electrical conductors and connections associated with additional pace/sense electrodes to the lead. The proximal coated portion and the distal coated portion of the defibrillation electrode may also decrease an amount of passive shunting that occurs in signals sensed by the medical device via the medical device lead.

In some examples, a medical electrical lead includes a lead body and a high voltage electrode positioned on the lead body, the high voltage electrode including a proximal coated portion, a distal coated portion, and an uncoated portion between the proximal coated portion and the distal coated portion, where the proximal coated portion and the distal coated portion are coated with an electrically insulating material configured to prevent conduction of signals having a first range of voltages between the high voltage electrode and patient tissue and allow conduction of signals having a second range of voltages between the high voltage electrode and the patient tissue, where the first range of voltages is lower than the second range of voltages. Additionally, the medical electrical lead includes a set of low voltage electrodes positioned on the lead body, the set of low voltage electrodes including a first low voltage electrode and a second low voltage electrode distal to the first low voltage electrode, where the set of low voltage electrodes and the uncoated portion are positioned on the lead body such that: a first angle is formed between a first line passing through the first low voltage electrode and the second low voltage electrode and a second line passing through the first low voltage electrode and the uncoated portion, and a second angle is formed between the first line and a third line passing through the second low voltage electrode and the uncoated portion.

In some examples, a medical device system includes a medical electrical lead including a lead body and a high voltage electrode positioned on the lead body, the high voltage electrode including a proximal coated portion, a distal coated portion, and an uncoated portion between the proximal coated portion and the distal coated portion, where the proximal coated portion and the distal coated portion are coated with an electrically insulating material configured to prevent conduction of signals having a first range of voltages between the high voltage electrode and patient tissue and allow conduction of signals having a second range of voltages between the high voltage electrode and the patient tissue, where the first range of voltages is lower than the second range of voltages. Additionally, the medical device system includes a set of low voltage electrodes positioned on the lead body, the set of low voltage electrodes including a first low voltage electrode and a second low voltage electrode distal to the first low voltage electrode, where the set of low voltage electrodes and the uncoated portion are positioned on the lead body such that a first angle is formed between a first line passing through the first low voltage electrode and the second low voltage electrode and a second line passing through the first low voltage electrode and the uncoated portion, and a second angle is formed between the first line and a third line passing through the second low voltage electrode and the uncoated portion. Additionally, the medical device system includes a medical device including sensing circuitry electrically coupled to the medical electrical lead, where the sensing circuitry is configured to one or more of: sense a first electrogram according to a first vector including the first low voltage electrode and the second low voltage electrode; sense a second electrogram according to a second vector including the first low voltage electrode and the uncoated portion; or sense a third electrogram according to a third vector including the second low voltage electrode and the uncoated portion.

In some examples, a medical electrical lead includes a lead body including a first curvilinear portion and a second curvilinear portion distal to the first curvilinear portion; a first high voltage electrode positioned on the first curvilinear portion of lead body, where the first high voltage electrode includes at least one coated portion that is coated with an electrically insulating material configured to prevent conduction of signals having a first range of voltages between the first high voltage electrode and patient tissue and allow conduction of signals having a second range of voltages between the first high voltage electrode and the patient tissue, where the first range of voltages is lower than the second range of voltages; a second high voltage electrode positioned on the second curvilinear portion of the lead body; and a set of low voltage electrodes positioned on the lead body, the set of low voltage electrodes including a first low voltage electrode and a second low voltage electrode distal to the first low voltage electrode, where the first low voltage electrode is positioned on the lead body proximal to the first high voltage electrode, and where the second low voltage electrode is placed on the lead body between the first high voltage electrode and the second high voltage electrode.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

This disclosure describes techniques for using a medical device lead having an arrangement of electrodes that provides a set of non-parallel electrode vectors. The medical device lead, in some cases, may include a set of electrodes including at least one defibrillation electrode and at least two pace/sense electrodes. The medical device lead may include at least one curvilinear portion such that the set of vectors form angles with one another. In some examples, a defibrillation electrode may be disposed along a curvilinear portion of the medical device lead such that the defibrillation electrode forms an arc, and may include an uncoated portion at or near the peak or apex of the arc configured to conduct relatively lower voltage signals, such as cardiac pacing pulses and sensed electrical signals from the heart, and thus form vectors with the pace/sense electrodes for pacing and sensing. In some examples, the first pace/sense electrode, the second pace/sense electrode, and the uncoated portion of the defibrillation electrode may form a triangle. In some examples, defibrillation electrodes may be referred to herein as "high voltage electrodes." In some examples, pace/sense electrodes may be referred to herein as "low voltage electrodes."

Figure 1A:
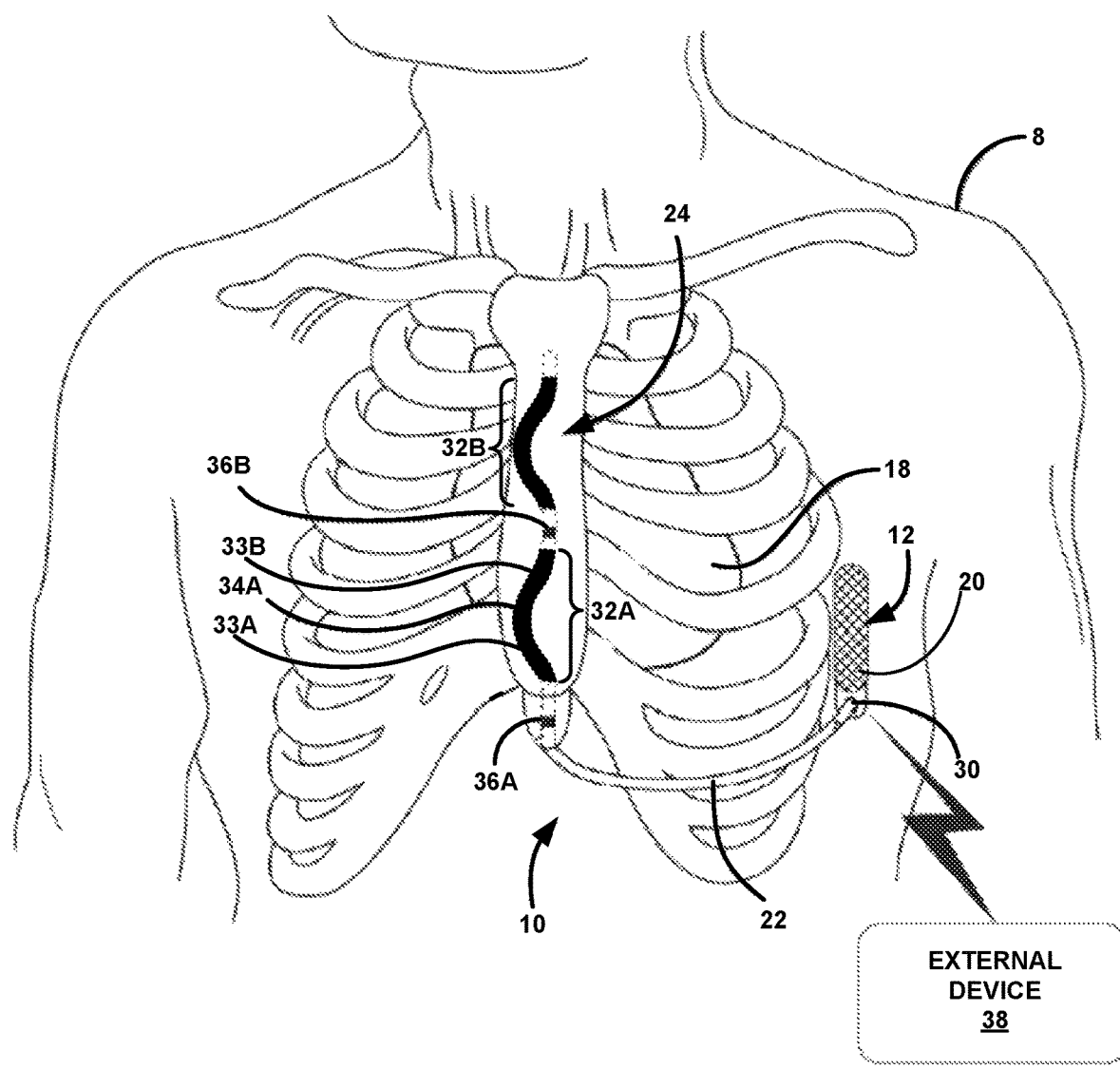
FIG. 1A is a conceptual drawing illustrating a front view of a patient with an example medical device system having a medical lead, in accordance with one or more techniques described herein.
Figure 1B:
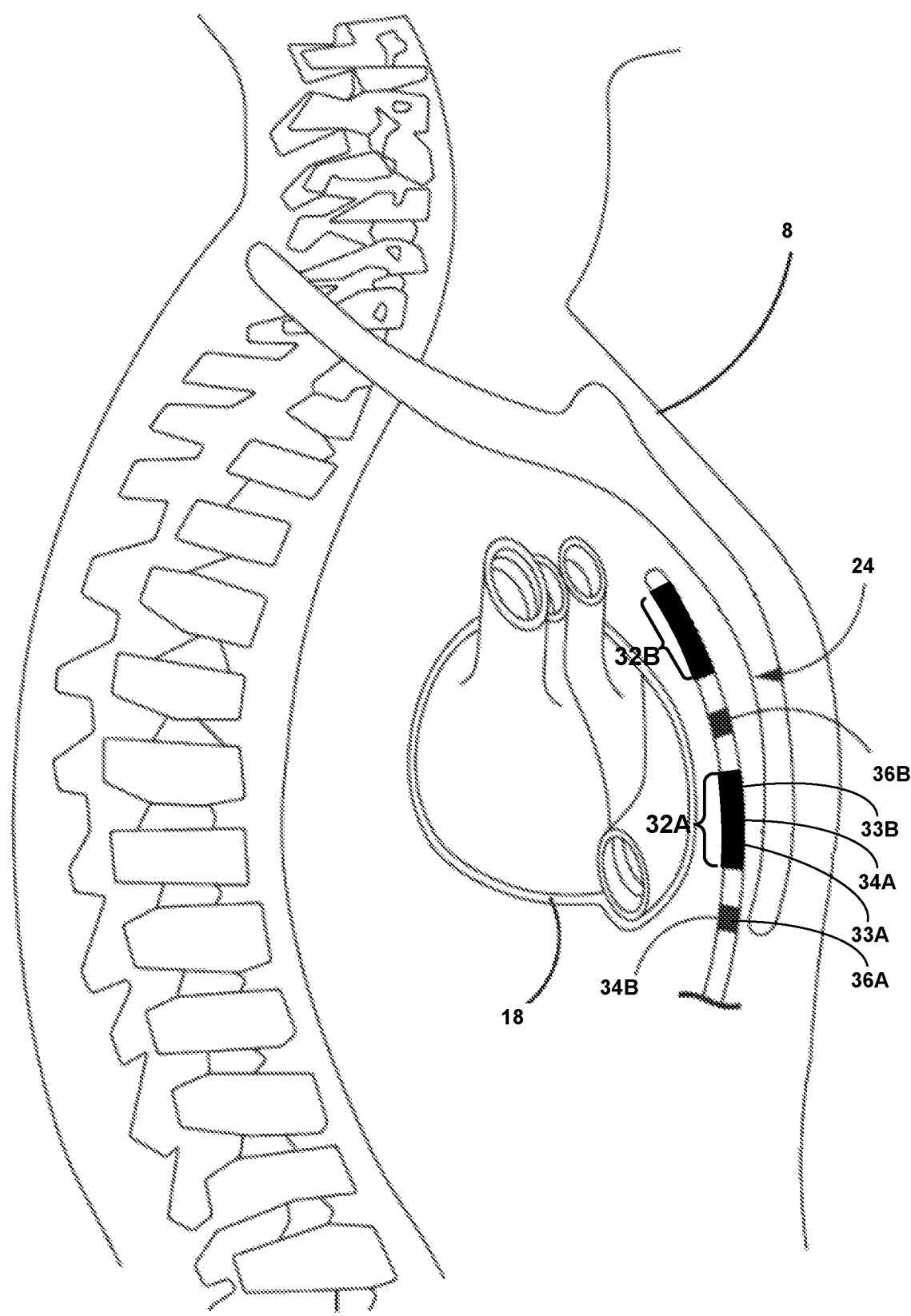
FIG. 1B is a conceptual drawing illustrating a side view of the patient with the example medical device system of FIG. 1A, in accordance with one or more techniques described herein.
Figure 1C:
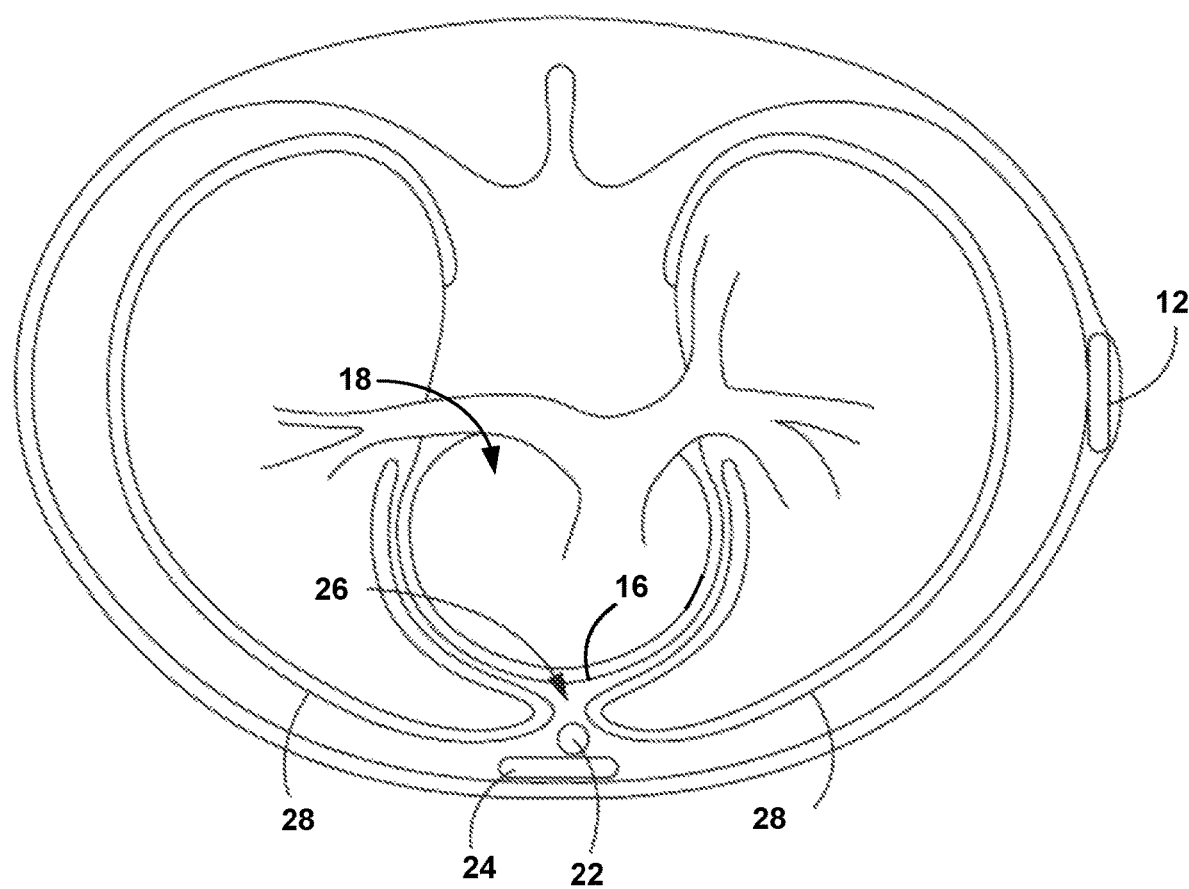
FIG. 1C is a conceptual drawing illustrating a transverse view of the patient with the example medical device system of FIG. 1A, in accordance with one or more techniques described herein.

FIGS. 1A-1C are conceptual diagrams of a medical device system 10 implanted within a patient 8. FIG. 1A is a front view of medical device system 10 implanted within patient 8. FIG. 1B is a side view of medical device system 10 implanted within patient 8. FIG. 1C is a transverse view of medical device system 10 implanted within patient 8.

In some examples, medical device system 10 is an extravascular implantable cardioverter-defibrillator (EV-ICD) system implanted within patient 8. However, the techniques described herein may be applicable to other implanted and/or external cardiac systems, including cardiac pacemaker systems, cardiac resynchronization therapy defibrillator (CRT-D) systems, cardioverter systems, wearable automated external defibrillator (WAED) systems, or combinations thereof, as well as other stimulation and/or sensing systems, such as neurostimulation systems. In addition, system 10 may not be limited to treatment of a human patient. In alternative examples, system 10 may be implemented in non-human patients, such as primates, canines, equines, pigs, bovines, ovines, felines, or the like. These other animals may undergo clinical or research therapies that may benefit from the subject matter of this disclosure.

IMD 12 is configured to be implanted in a patient, such as patient 8. In some examples, IMD 12 is implanted subcutaneously or submuscularly on the left midaxillary of patient 8, such that IMD 12 may be positioned on the left side of patient 8 above the ribcage. In some other examples, IMD 12 may be implanted at other subcutaneous locations on patient 8 such as at a pectoral location or abdominal location. IMD 12 includes housing 20 that may form a hermetic seal that protects components of IMD 12. In some examples, housing 20 of IMD 12 may be formed of a conductive material, such as titanium, or of a combination of conductive and non-conductive materials, which may function as a housing electrode. IMD 12 may also include a connector assembly (also referred to as a connector block or header) that includes electrical feedthroughs through which electrical connections are made between lead 22 and electronic components included within the housing. Housing 20 may house one or more of processing circuitry, memories, transmitters, receivers, sensors, sensing circuitry, therapy circuitry, power sources and other appropriate components.

In general, medical device systems (e.g., system 10) may include one or more medical devices, leads, external devices, or other components configured to implement the techniques described herein. In the example illustrated in FIG. 1A, IMD 12 is connected to one implantable cardiac lead 22. In other examples, two or more leads may be connected to IMD 12. In some examples, IMD 12 may be configured to deliver high-energy anti-tachyarrhythmia (e.g., cardioversion or defibrillation) shocks to heart 18 when a ventricular tachyarrhythmia, e.g., ventricular tachycardia (VT) or ventricular fibrillation (VF), is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by IMD 12.

Lead 22 includes an elongated lead body having a proximal end that includes a connector 30 configured to be connected to IMD 12 and a distal portion that includes electrodes 32A, 32B, 36A, and 36B (collectively, "electrodes 32, 36"). Lead 22 extends subcutaneously above the ribcage from IMD 12 toward a center of the torso of patient 8. At a location near the center of the torso, lead 22 bends or turns and extends intrathoracically superior posterior to sternum 24. Lead 22 thus may be implanted at least partially in a substernal space, such as at a target site between the ribcage or sternum 24 and heart 18. In one such configuration, a proximal portion of lead 22 may be configured to extend subcutaneously from IMD 12 toward sternum 24 and a distal portion of lead 22 may be configured to extend superior posterior to sternum 24 in the anterior mediastinum 26 (FIG. 1C). Lead 22 may include one or more curved sections as discussed herein to configure lead 22 to naturally (e.g., in a self-biasing manner) extend in this way upon deployment.

For example, lead 22 may extend intrathoracically superior posterior to sternum 24 within anterior mediastinum 26. Anterior mediastinum 26 may be viewed as being bounded posteriorly by pericardium 16, laterally by pleurae 28, and anteriorly by sternum 24. In some examples, the anterior wall of anterior mediastinum 26 may also be formed by the transversus thoracis and one or more costal cartilages. Anterior mediastinum 26 includes a quantity of loose connective tissue (such as areolar tissue), some lymph vessels, lymph glands, substernal musculature (e.g., transverse thoracic muscle), and small vessels or vessel branches. In one example, the distal portion of lead 22 may be implanted substantially within the loose connective tissue and/or substernal musculature of anterior mediastinum 26. In such examples, the distal portion of lead 22 may be physically isolated from pericardium 16 of heart 18. A lead implanted substantially within anterior mediastinum 26 may be referred to herein as a substernal lead. Electrical therapy, such as anti-arrhythmia pacing, cardioversion or defibrillation, provided by lead 22 implanted substantially within anterior mediastinum 26 may be referred to herein as substernal electrical therapy, substernal pacing, substernal cardioversion, or substernal defibrillation.

The distal portion of lead 22 is described herein as being implanted substantially within anterior mediastinum 26. Thus, some of distal portion of lead 22 may extend out of anterior mediastinum 26 (e.g., a proximal end of the distal portion), although much of the distal portion may be positioned within anterior mediastinum 26. In other examples, the distal portion of lead 22 may be implanted intrathoracically in other non-vascular, extra-pericardial locations, including the gap, tissue, or other anatomical features around the perimeter of and adjacent to, but not attached to, the pericardium 16 or other portion of heart 18 and not above sternum 24 or the ribcage. As such, lead 22 may be implanted anywhere within the "substernal space" defined by the undersurface between the sternum and/or ribcage and the body cavity but not including pericardium 16 or other portions of heart 18. The substernal space may alternatively be referred to by the terms "retrosternal space" or "mediastinum" or "infrasternal" and may include the anterior mediastinum 26. In other words, the distal portion of lead 22 may be implanted in the region around the outer surface of heart 18, but not attached to heart 18. For example, the distal portion of lead 22 may be physically isolated from pericardium 16.

Lead 22 may include an insulative lead body having a proximal end that includes connector 30 configured to be connected to IMD 12 and a distal portion that includes one or more electrodes. As shown in FIG. 1A, the one or more electrodes of lead 22 may include electrodes 32A, 32B, 36A, and 36B although in other examples, lead 22 may include more or fewer electrodes. Lead 22 also includes one or more conductors that form an electrically conductive path within the lead body and interconnect the electrical connector and respective ones of the electrodes. In some cases, lead 22 includes a first conductor electrically coupled to defibrillation electrode 32A, a second conductor electrically coupled to defibrillation electrode 32B, a third conductor electrically coupled to pace/sense electrode 36A, and a fourth conductor electrically coupled to pace/sense electrode 36B. In some examples, a proximal end of the first conductor, a proximal end of the second conductor, a proximal end of the third conductor, and a proximal end of the fourth conductor may be coupled to sensing circuitry and/or signal generation circuitry within housing 20 of IMD 12 via interconnects in the connector 30.

Electrodes 32A, 32B may be defibrillation electrodes (individually or collectively "defibrillation electrode(s) 32"). Although electrodes 32 may be referred to herein as "defibrillation electrodes 32," electrodes 32 may be configured to deliver other types of anti-tachyarrhythmia shocks, such as cardioversion shocks. In some examples, defibrillation electrodes 32A, 32B may functionally be different sections of a single defibrillation electrode 32, such that both defibrillation electrodes 32 are coupled to the same conductor or are otherwise configured to provide the same electrical therapy. Additionally, in some examples, defibrillation electrodes 32A, 32B may each be coupled to different conductors. In such examples, defibrillation electrodes 32A, 32B may be configured to provide electrical therapy together or separately via switches within IMD 12. Although defibrillation electrodes 32 are depicted in FIGS. 1A-1C as coil electrodes, it is to be understood that defibrillation electrodes 32 may be of other configurations in other examples. Defibrillation electrodes 32 may be located on the distal portion of lead 22, where the distal portion of lead 22 is the portion of lead 22 that is configured to be implanted to extend along sternum 24.

Defibrillation electrodes 32 may, in some cases, may include one or more portions that are coated with an electrically insulating material. Defibrillation electrode portions that are coated with at least one electrically insulating material may be referred to herein as "coated portions." Additionally, in some cases, defibrillation electrodes 32 may each include one or more portions that are not coated with an electrically insulating material. Defibrillation electrode portions that are not coated with an electrically insulating material may be referred to herein as "uncoated portions." In some cases, an entire surface area of a defibrillation electrode of defibrillation electrodes 32 may be coated. In some cases, an entire surface area of a defibrillation electrode of defibrillation electrodes 32 may be uncoated.

In the example illustrated in FIGS. 1A-1C, defibrillation electrode 32A includes a proximal coated portion 33A, a distal coated portion 33B, and an uncoated portion 34 between proximal coated portion 33A and distal coated portion 33B. In some examples, uncoated portion 34 is a first uncoated portion, proximal coated portion 33A is a first proximal uncoated portion, and distal coated portion 33B is a first distal uncoated portion. In some such examples, defibrillation electrode 32B includes a second proximal coated portion, a second distal coated portion, and a second uncoated portion between the second proximal coated portion and the second distal coated portion. In other examples, however, one of defibrillation electrodes 32A or 32B may not include any coated portion, but instead be entirely uncoated, or may not include any uncoated portion, and be entirely coated. In another example, neither of the defibrillation electrodes 32A or 32B may include coated and uncoated portions. Instead, one defibrillation electrode 32 (e.g., defibrillation electrode 32A) may be entirely coated and the other one of defibrillation electrodes 32 (e.g., defibrillation electrode 32B) may be entirely uncoated. For each of defibrillation electrodes 32, a "proximal" coated portion may be more proximal on lead 22 (e.g., more proximal to connector 30) than a "distal" coated portion.

In some examples, the electrically insulating material which coats proximal coated portion 33A and distal coated portion 33B (collectively, "coated portions 33") prevents conduction of relatively lower voltage signals between coated portions 33 and tissue of patient 8. Additionally, the electrically insulating material may allow conduction of relatively higher voltage signals between coated portions 33 and tissue of patient 8. Uncoated portion 34 may be configured to both allow conduction of relatively lower voltage signals and allow conduction of relatively higher voltage signals. For example, coated portions 33 may be configured to prevent transmission of a pacing pulse, prevent sensing of a cardiac depolarization, and allow transmission of a defibrillation shock. Uncoated portion 34, on the other hand, may be configured to transmit a defibrillation shock, transmit a pacing pulse, sense an electrical signal corresponding to a cardiac depolarization, or any combination thereof. As such, an entire length of a defibrillation electrode such as defibrillation electrode 32A may be configured to conduct a defibrillation shock delivered by signal generation circuitry within housing 20, and a portion (e.g., uncoated portion 34)

of defibrillation electrode 32A may be configured to transmit pacing pulses and sense cardiac depolarizations or other relatively lower voltage electrical signals. In this way, uncoated portion 34 of defibrillation electrodes 32 may perform at least some of the same functionalities as pace/sense electrodes 36. Coated portions 33 may, in some cases, prevent or decrease an extent of passive shunting by an electrode 32 during sensing of cardiac electrograms by IMD 12 via other electrodes of lead 22, e.g., electrodes 36.

The electrically insulating material may, in some examples, extend around the entire circumference of coated portions 33 of defibrillation electrodes 32. The electrically insulating material may be any of a number of material such as single or combinations of tantalum pentoxide, titanium oxides, zirconium oxide, vanadium oxide, niobium oxide, doped silicon, silicon dioxide, boron doped diamond, doped glass, ceramic coating or polymer composite or other material that has the property of substantially preventing the transmission or delivery of low voltages while not substantially preventing the transmission or delivery of high voltages. A thickness of the electrically insulating material may vary based on a type of material that defibrillation electrodes 32 are made of, the type of electrically insulating material, dimensions of the respective coated portion 33, an expected depth and position of the distal portion of lead 22, e.g., substernal or subcutaneous location. In examples where tantalum pentoxide is the electrically insulating material, the thickness of the electrically insulating material may be within a range from 0.2 micrometers ($\mu$m) to less than or equal to 2.0 $\mu$m. However, other thicknesses may be utilized without departing from the scope of this disclosure. In one example, coated portions 33 are coated with tantalum pentoxide having a thickness within a range from 0.6 $\mu$m to 0.9 $\mu$m microns. In such an example, the tantalum pentoxide coating significantly blocks current flow up to 90V, thus preventing the sensing of cardiac depolarization events and preventing the transmission of pacing pulses. Additionally, in such an example, electrical signals having voltages higher than 90V (e.g., defibrillation shocks) overcome the electrically insulating property of the tantalum pentoxide coating and may conduct through coated portions 33 of defibrillation electrodes 32.

Coated portions 33 and uncoated portion 34 may vary in size. In some examples, uncoated portion 34 may be less than or equal to 25% of the length of defibrillation electrode 32A. Additionally, in some examples, uncoated portion 34 may be less than or equal to 10% of the length of defibrillation electrode 32A. Uncoated portion 34 may, in some examples, have a surface area that is less than or equal to 100 millimeters squared ($mm^2$). In other instances, uncoated portion 34 may have a surface area that is less than or equal to 10 $mm^2$. Uncoated and coated portions may have sizes other than those described above.

Lead 22 may be implanted at a target site posterior to sternum 24 such that a therapy electrode vector is substantially across a ventricle of heart 18, substantially across an atrium of heart 18, or substantially across both of a ventricle and an atrium of heart 18. In some examples, a therapy vector may be between defibrillation electrodes 32 and a housing electrode formed by or on IMD 12, as discussed further below. The therapy electrode vector may, in one example, be viewed as a line that extends from a point on defibrillation electrodes 32 (e.g., a center of one of the defibrillation electrodes 32) to a point on a housing electrode of IMD 12. As such, it may be advantageous to increase an amount of area across which defibrillation electrodes 32 (and therein the distal portion of lead 22) extends across heart 18. Accordingly, lead 22 may be configured to define a curvilinear distal portion as depicted in FIG. 1A. In some examples, the curvilinear distal portion of lead 22 may help improve the efficacy and/or efficiency of pacing, sensing, and/or defibrillation to heart 18 by IMD 12, in addition to the techniques for controlling the delivery of cardiac therapy described herein.

The defibrillation electrodes 32A, 32B may be electrically connected to one or more conductors, which may be disposed in a body wall of the lead 22 and/or may be disposed in one or more insulated lumens (not shown) defined by the lead 22. In some examples, each of the defibrillation electrodes 32A, 32B is connected to a common conductor such that IMD 12 may apply a voltage simultaneously to all the defibrillation electrodes 32A, 32B to deliver a defibrillation shock to a patient's heart (e.g., heart 18). In some examples, the defibrillation electrodes 32A, 32B may be attached to separate conductors such that IMD 12 may apply a voltage to each defibrillation electrode 32 independent of the other defibrillation electrodes 32. In this case, IMD 12 or lead 22 may include one or more switches or other mechanisms to electrically connect the defibrillation electrode segments to the same or different voltage sources.

Housing 20 may be charged with or function as a polarity different than the polarity of the one or more defibrillation electrodes 32 and/or pace/sense electrodes 36 such that electrical energy may be delivered between the housing 20 and the defibrillation electrodes 32 and/or pace/sense electrodes 36 to heart 18. Each defibrillation electrode 32 may have the same polarity as every other defibrillation electrode 32 when a voltage is applied to it such that a defibrillation shock may be delivered from each of defibrillation electrodes 32 to housing 20. In examples in which defibrillation electrodes 32 are electrically connected to a common conductor within lead body 12, this is the only configuration of defibrillation electrodes 32. However, in other examples, defibrillation electrodes 32 may be coupled to separate conductors within lead body 22 and may therefore each have different polarities such that electrical energy may flow between defibrillation electrodes 32, or between one or more of defibrillation electrodes 32 and an electrode on housing 20.

Pace/sense electrodes 36A and 36B (collectively, "pace/sense electrodes 36") may be located on the distal portion of lead 22. Electrodes 36 may be referred to herein as pace/sense electrodes as they generally are configured for use in delivery of pacing pulses and/or sensing of cardiac electrical signals. In some instances, electrodes 36 may provide only pacing functionality, only sensing functionality, or both pacing functionality and sensing functionality. Pace/sense electrode 36A and pace/sense electrode 36B may be separated by defibrillation electrode 32A. In examples in which lead 22 includes more or fewer electrodes 32, 36, such electrodes may be positioned at other locations on lead 22. In some examples, IMD 12 may include one or more electrodes 32, 36 on another lead (not shown). Other lead configurations may be used, such as various electrode arrangements. For example, one or more pace/sense electrodes 36 may be placed between two defibrillation electrodes 32, such as described above. In an example, multiple pace/sense electrodes 36 may be placed between two defibrillation electrodes 32. In an example, two defibrillation electrodes 32 may be adjacent (e.g., such that the two defibrillation electrodes 32 are not separated by any pace/sense electrodes 36 between the two defibrillation electrodes 32). Other arrangements may additionally or alternatively be used.

Lead 22 may define different sizes and shapes as may be appropriate for different purposes (e.g., for different patients or for different therapies). As discussed above, in some examples, the distal portion of lead 22 may have a curvilinear portion that includes one or more curved sections. As shown in the example of FIG. 1A, the distal portion of lead 22 is a curvilinear shape that includes two "C" shaped curves, which together may resemble the Greek letter epsilon, "ε." Defibrillation electrodes 32 are each carried by one of the two respective C-shaped curved portions of the lead body distal portion. The two C-shaped curves extend or curve in the same direction away from a central axis of the lead body. In some examples, pace/sense electrodes 36 may be substantially aligned with the central axis of the distal portion of lead 22. In such examples, mid-points of defibrillation electrodes 32 are laterally offset from pace/sense electrodes 36. In some examples, the central axis of the distal portion of lead 22 represents a line that passes through each pace/sense electrode of pace/sense electrodes 36. Other examples of extra-cardiovascular leads including one or more defibrillation electrodes 32 and one or more pace/sense electrodes 36 carried by the curvilinear (e.g., curving, serpentine, undulating or zig-zagging) distal portion of lead 22 also may be implemented using the techniques described herein. In some examples, the distal portion of lead 22 may be straight (e.g., straight or nearly straight).

In some examples, the electrode arrangement on lead 22 may correspond to a geometry of lead 22. For example, pace/sense electrodes 36 may be positioned on relative peaks of a curved lead shape, while defibrillation electrodes 32 may be positioned on relative valleys of the curved lead shape. The relative valleys may, in some cases, represent curvilinear portions of lead 22. Additionally, uncoated portion 34 may be positioned at the "bottoms" of the respective curvilinear portions or valleys. In other examples, the distal portion of lead 22 may include branches, biased portions expanding away from a central shaft, or other shapes (e.g., with one or more of electrodes 32, 36 disposed on the branches, shaft, or biased portions) that may provide appropriate monitoring information or therapy. Deploying lead 22 such that electrodes 32, 36 are thusly at these depicted peaks and valleys of the curvilinear shape of the distal portion of lead 22 may therein increase an efficacy of system 10. For example, electrodes 32, 36 may provide access to better sensing or therapy vectors when lead 22 is deployed into the curvilinear shape, in addition to the techniques for controlling the delivery of cardiac therapy described herein.

Orienting the curvilinear-shaped lead such that pace/sense electrodes 36 are closer to heart 18 may provide better electrical sensing of the cardiac signal and/or lower pacing capture thresholds than if pace/sense electrodes 36 were oriented further from heart 18. The curvilinear or other shape of the distal portion of lead 22 may have increased fixation to patient 8 as a result of the shape providing resistance against adjacent tissue when an axial force is applied. Another advantage of a shaped distal portion is that pace/sense electrodes 36 may have access to greater surface area over a shorter length of heart 18 relative to a lead having a straighter distal portion.

In some examples, the elongated lead body of lead 22 may have a diameter within a range from 3 French (Fr) to 12 Fr, although lead bodies having diameters less than 3 Fr and more than 12 Fr may also be utilized. In another example, the distal portion and/or other portions of the lead body may have a flat, ribbon or paddle shape. In such examples, the width across the flat portion of the flat, ribbon or paddle shape may be between 1 and 3.5 mm. Other lead body designs may be used without departing from the scope of this disclosure. The lead body of lead 22 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

In some examples, defibrillation electrodes 32 may have a length within a range from 2 centimeters (cm) to 16 cm. In some examples, defibrillation electrodes 32 may be a flat ribbon electrode, paddle electrode, braided or woven electrode, mesh electrode, segmented electrode, directional electrode, patch electrode or other type of electrode besides an elongated coil electrode.

Pace/sense electrodes 36 may include ring electrodes, short coil electrodes, hemispherical electrodes, segmented electrodes, directional electrodes, or the like. In some examples, pace/sense electrodes 36 may have substantially the same outer diameter as the lead body. In one example, pace/sense electrodes 36 may have surface areas within a range from 1 millimeter squared ($mm^2$) to 55 $mm^2$. Pace/sense electrodes 36 may, in some examples, have relatively the same surface area or different surface areas. Depending on the configuration of lead 22, pace/sense electrodes 36 may be spaced apart by the length of defibrillation electrodes 32, plus some insulated length on each side of defibrillation electrode 32, e.g., within a range from 2 cm to 16 cm. In other examples, such as when a pair of pace/sense electrodes 36 are not separated by a defibrillation electrode 32, the electrode spacing may be smaller, e.g., up to 2 cm. The example dimensions provided above are exemplary in nature and should not be considered limiting of the examples described herein.

In some examples, IMD 12 may include one or more housing electrodes (not shown) positioned on housing 20 of IMD 12. Such housing electrodes may be formed integrally with an outer surface of hermetically-sealed housing 20 of IMD 12, or otherwise may be coupled to housing 20. In some examples, a housing electrode may be defined by an uninsulated portion of an outward facing portion of housing 20 of IMD 12. In some examples, housing 20 may define one or more additional housing electrodes, which may be defined by corresponding divisions between insulated and uninsulated portions of housing 20. In still other examples, substantially all of housing 20 may be uninsulated, such that substantially all of housing 20 defines a housing electrode.

In general, system 10 may sense electrical signals, such as via one or more vectors that include combinations of uncoated portion 34 of defibrillation electrodes 32, pace/sense electrodes 36, and/or a housing electrode of IMD 12. The sensed electrical intrinsic signals may include electrical signals generated by cardiac muscle and indicative of depolarizations and repolarizations of heart 18 at various times during the cardiac cycle. IMD 12 may be configured to analyze the electrical signals sensed by the one or more vectors to detect an arrhythmia, such as ventricular tachycardia (VT), ventricular fibrillation (VF), atrial tachycardia (AT), atrial fibrillation (AF), or any combination thereof. In response to detecting the arrhythmia, in some cases, IMD 12 may begin to charge a storage element, such as a bank of one or more capacitors. When the capacitors are charged, IMD 12 may deliver substernal electrical therapy, e.g., antitachycardia pacing (ATP), cardioversion or defibrillation shocks, bradycardia pacing, asystole pacing, and/or post-shock pacing. In some examples, IMD 12 may generate and deliver bradycardia pacing in addition to ATP, cardioversion or defibrillation shocks, and/or post-shock pacing.

In some examples, system 10 may include external device 38. External device 38 may be a computing device that is configured for use in a home, ambulatory, clinic, or hospital setting to communicate with IMD 12 via wireless telemetry. Examples of communication techniques used by IMD 12 and external device 38 include radiofrequency (RF) telemetry, which may include an RF link established via Bluetooth®, wireless local networks, or medical implant communication service (MICS). The communication may include one-way communication in which one device is configured to transmit communication messages and the other device is configured to receive those messages. Alternatively, or additionally, the communication may include two-way communication in which each device is configured to transmit and receive communication messages.

External device 38 may include communication circuitry configured to communicate with one or more devices of system 10 (e.g., IMD 12) in accordance with the techniques described above. For example, external device 38 may be used to program commands or operating parameters of IMD 12 for controlling functioning of IMD 12 when external device 38 is configured as a programmer for IMD 12. External device 38 may be used to communicate with IMD 12 to retrieve data such as operational data, physiological data accumulated in IMD memory, or the like. As such, external device 38 may function as a programmer for IMD 12, an external monitor for IMD 12, or a consumer device such as a smartphone. External device 38 may be coupled to a remote patient monitoring system, such as CARELINK® Network, available from Medtronic plc, of Dublin, Ireland. In other examples, a clinician may use external device 38 to program or update therapy parameters that define cardiac therapy, and/or program or update modifications to the cardiac therapy parameters, sensing parameters, and/or electrode vectors associated with the plurality of heart position states, or perform other activities with respect to IMD 12. The clinicians may be a physician, technician, surgeon, electrophysiologist, or other healthcare professional. In some examples, the user may be patient 8.

Although described herein in the context of example IMD 12, the techniques for controlling the delivery of cardiac therapy described herein may be implemented with other types of IMD configured to deliver cardiac therapy. In some examples, the techniques described herein may be implemented with an external defibrillation device, or other devices or systems configured to deliver cardiac therapy. Although in the examples illustrated in FIGS. 1A-1C, lead 22 may be implanted substernally, in some examples, lead 22 may be implanted at other extracardiovascular locations including subcutaneously or submuscularly anterior to the sternum and/or the rib cage.

Figure 2:
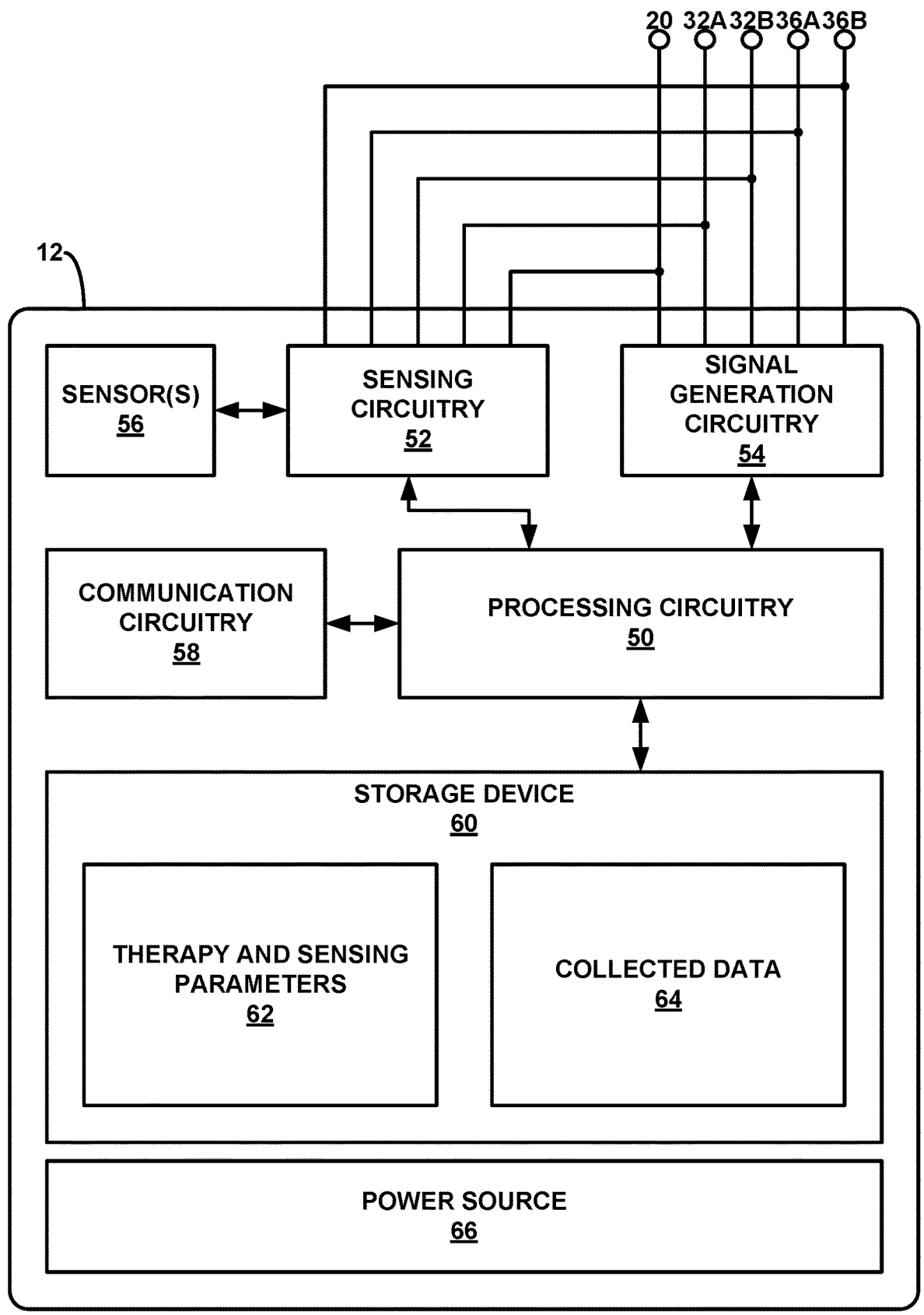
FIG. 2 is a functional block diagram illustrating an example configuration of the implantable medical device (IMD) of FIGS. 1A-1C, in accordance with one or more techniques described herein.

FIG. 2 is a functional block diagram illustrating an example configuration of IMD 12, in accordance with one or more techniques described herein. As shown in FIG. 2, IMD 12 includes processing circuitry 50, sensing circuitry 52, signal generation circuitry 54, sensors 56, communication circuitry 58, and storage device 60. Storage device 60 may store therapy and sensing parameters 62 and collected data 64. In addition, IMD 12 is electrically coupled to one or more electrodes 20, 32A, 32B, 36A, and 36B.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 monitors electrical cardiac signals from any combination of electrodes 20, 32A, 32B, 36A, and 36B, the various combinations of electrodes 20, 32A, 32B, 36A, and 36B forming a set of electrode vectors. In some examples, sensing circuitry 52 may include one or more amplifiers, filters, and analog-to-digital converters. For example, sensing circuitry 52 may include one or more detection channels, each of which may include an amplifier. The detection channels may be used to sense cardiac signals, such as a cardiac EGM. The channels may detect cardiac EGM signals from a particular combination (e.g., a vector) of electrodes 20, 32A, 32B, 36A, and 36B. Some detection channels may detect events, such as R-waves, P-waves, and T-waves and provide indications of the occurrences of such events to processing circuitry 50. One or more other detection channels may provide signals to an analog-to-digital converter (ADC), for conversion into a digital signal for processing, analysis, storage, or output by processing circuitry 50.

Each detection channel of sensing circuitry 52 may include a filter configured to pass a custom range of frequency values. For example, sensing circuitry 52 may include one or more narrow band channels, each of which may include a narrow band filtered sense-amplifier. Additionally, or alternatively, sensing circuitry 52 may include one or more wide band channels, each of which include an amplifier with a relatively wider pass band than the narrow band channels. Signals sensed by the narrow band channels and the wide band channels of sensing circuitry 52 may be converted to multi-bit digital signals by an ADC provided by, for example, sensing circuitry 52 or processing circuitry 50. In some examples, processing circuitry 50 analyzes the digitized version of signals from sensing circuitry 52. In other examples, processing circuitry 50 stores the digitized versions of the signals in storage device 60 (e.g., as collected data 64), outputs the digitized versions of the signals via communication circuitry 58, or any combination thereof. Thresholds, filter parameter values, blanking intervals, and other parameter values for controlling the sensing and processing of cardiac signals by sensing circuitry 52 and processing circuitry 50 may be stored as therapy and sensing parameters 62 in storage device 60.

Generally, processing circuitry 50 controls signal generation circuitry 54 to deliver therapy to heart 18 of patient 8 according to selected values of therapy and sensing parameters 62, which may be stored storage device 60. As an example, processing circuitry 50 may control signal generation circuitry 54 to deliver electrical pulses with the amplitudes, pulse widths, frequency, and/or electrode polarities (which define a therapy vector) specified by the therapy and sensing parameters 62. Therapy and sensing parameters 62 stored in storage device 60 may include thresholds or other conditions, which may be compared to parameters of the EGM, and based on which processing circuitry 50 controls signal generation circuitry 54 to deliver therapy, such as cardiac rates, intervals, and/or EGM morphology parameters.

Signal generation circuitry 54 is configured to generate and deliver electrical therapy to patient 8. As shown in FIG. 2, signal generation circuitry 54 is electrically coupled to electrodes 20, 32A, 32B, 36A, and 36B, e.g., via conductors within the respective lead 22 and, in the case of electrodes disposed on housing 20 of IMD 12, within housing 20. For example, signal generation circuitry 54 may deliver pacing, defibrillation or cardioversion pulses to heart 18 via at least two of electrodes 20, 32A, 32B, 36A, and 36B. In some examples, signal generation circuitry 54 delivers therapy in the form of signals other than pulses such as sine waves, square waves, or other substantially continuous time signals. In some examples, signal generation circuitry 54 may include one or more capacitors, charge pumps, current sources, or other signal generation circuitry.

Sensing circuitry 52 and signal generation circuitry 54 may be selectively coupled to electrodes 20, 32A, 32B, 36A, and 36B, e.g., via switching circuitry (not illustrated in FIG. 2) as controlled by processing circuitry 50. The switching circuitry may include one or more transistors or other circuitry for selectively coupling electrodes 20, 32A, 32B, 36A, and 36B to other circuitry of IMD 12. Sensing circuitry 52 may monitor signals from electrodes 20, 32A, 32B, 36A, and 36B in order to monitor electrical activity of heart (e.g., to detect depolarizations for heart rate determination and/or to produce a cardiac electrogram for morphological or other analyses).

Sensor(s) 56 may include one or more accelerometers. Sensors 56 may additionally or alternatively include other sensors such as gyrometers, magnetometers, barometers, acoustic sensors, pressure sensors, flow sensors, oxygen ($O_2$) saturation sensors. Information obtained from sensor(s) 56 may be used to determine activity level, posture, blood pressure, blood flow, blood oxygen level, or respiratory rate, as examples. In some examples, this information may be used by processing circuitry 50 to aid in the classification of an abnormal heart rhythm. In some examples, at least some of sensor(s) 56 may be located outside of the housing 20 of IMD 12. Sensor(s) 56 may be located on a lead (e.g., lead 22) that is coupled to IMD 12 or may be implemented in a remote sensor that wirelessly communicates with IMD 12 via communication circuitry 58. In any case, sensor(s) 56 are electrically or wirelessly coupled to circuitry contained within housing 20 of IMD 12.

Communication circuitry 58 may include any suitable hardware, firmware, software or any combination thereof for communicating with another device, such as external device 38. Under the control of processing circuitry 50, communication circuitry 58 may receive downlink telemetry from, as well as send uplink telemetry to, external device 38 or another device. In some examples, communication circuitry 58 exchanges information with the aid of an internal or external antenna (not illustrated in FIG. 2). In addition, processing circuitry 50 may communicate with a networked computing device via an external device (e.g., external device 38) and a computer network, such as the Medtronic CareLink® Network developed by Medtronic, plc, of Dublin, Ireland. Communication circuitry 58 may include any combination of a Bluetooth® radio, an electronic oscillator, frequency modulation circuitry, frequency demodulation circuitry, amplifier circuitry, and power switches such as a metal-oxide-semiconductor field-effect transistors (MOSFET), a bipolar junction transistor (BJT), an insulated-gate bipolar transistor (IGBT), a junction field effect transistor (JFET), or another element that uses voltage for its control.

Storage device 60 may be configured to store information within IMD 12 during operation. Storage device 60 may include a computer-readable storage medium or computer-readable storage device. In some examples, storage device 60 includes one or more of a short-term memory or a long-term memory. Storage device 60 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 60 is used to store data indicative of instructions for execution by processing circuitry 50.

In some examples, IMD 12 may be configured to sense, using sensing circuitry 52, cardiac signals according to a selected one or more of set of vectors. Processing circuitry 50 may control sensing circuitry 52 to obtain, for each vector of the set of vectors, data corresponding to a difference in electric potential between nodes of the respective vector. Nodes of each vector may correspond to a pair of electrodes 20, 32A, 32B, 36A, and 36B, or more than two electrodes 20, 32A, 32B, 36A, and 36B if two of the electrodes are connected as a common node. Each of electrodes 20, 32A, 32B, 36A, and 36B, including electrodes 32, 36 may be coupled to sensing circuitry 52 via a respective electrical conductor. In this way, IMD 12 may be able to obtain a signal (e.g., a signal indicative of an electric potential) using each electrode of electrodes 20, 32A, 32B, 36A, and 36B. A vector may be defined by a set of parameters including a combination of two or more electrodes, a spatial arrangement of the two or more electrodes, and a polarity of each electrode of the two or more electrodes.

For example, processing circuitry 50 may be configured to control sensing circuitry 52 to obtain a first electrogram via a first vector including first pace/sense electrode 36A and second pace/sense electrode 36B. In some examples, the first electrogram is proportional to a difference in electric potential between first pace/sense electrode 36A and second pace/sense electrode 36B. Additionally, processing circuitry 50 may be configured to control sensing circuitry 52 to obtain a second electrogram via a second vector including first pace/sense electrode 36A and uncoated portion 34 of first defibrillation electrode 32A. In some examples, the second electrogram is proportional to a difference in electric potential between first pace/sense electrode 36A and uncoated portion 34. The second vector may form a first angle with the first vector. In other words, a line which passes through first pace/sense electrode 36A and second pace/sense electrode 36B may form the first angle with a line that passes through first pace/sense electrode 36A and uncoated portion 34. In some examples, the first angle is within a range from thirty degrees to sixty degrees. However, the first angle is not meant to be limited to such a range. In some cases, the first angle may be less than thirty degrees or greater than sixty degrees.

Since cardiac depolarizations are directional in nature and follow a three-dimensional path through heart 18 of patient 8, it may be beneficial for the first vector to form an angle with the second vector such IMD 12 may be able obtain different angular perspectives of directional cardiac depolarizations, e.g., allowing selection of one of the vectors providing a preferred signal characteristics.

Additionally, processing circuitry 50 may control sensing circuitry 52 to obtain a third electrogram via a third vector including second pace/sense electrode 36B and uncoated portion 34 of first defibrillation electrode 32A. In some examples, the third electrogram is proportional to a difference in electric potential between second pace/sense electrode 36B and uncoated portion 34. The third vector may form a second angle with the first vector. In other words, a line which passes through first pace/sense electrode 36A and second pace/sense electrode 36B may form the second angle with a line that passes through second pace/sense electrode 36B and uncoated portion 34. In some examples, the second angle is within a range from thirty degrees to sixty degrees. However, the second angle is not meant to be limited to such a range. In some cases, the second angle may be less than thirty degrees or greater than sixty degrees. It may be beneficial for the third vector to form an angle with the first vector such that IMD 12 may obtain another angular perspective of the directional cardiac depolarizations in addition to the perspectives provided by the first vector and the second vector. Additionally, the second vector and the third vector may form an angle (e.g., within a range from 30 to 120 degrees) such that the first vector, the second vector, and the third vector form a triangle between first pace/sense electrode 36A, second pace/sense electrode 36B, and uncoated portion 34.

First pace/sense electrode 36A, second pace/sense electrode 36B, and uncoated portion 34 may, in some cases, be proximate to a ventricle of heart 18. In some cases, processing circuitry 50 may store one or more of the first electrogram, the second electrogram, and the third electrogram in storage device 60 as a part of collected data 64, where the first electrogram, the second electrogram, and the third electrogram are different.

In addition to being configured to selectively determine data corresponding to the first vector, the second vector, and/or the third vector which are located proximate to the ventricles of heart 18, processing circuitry 50 may be configured to direct sensing circuitry 52 to collect data via electrodes that are proximate to the atria of heart 18. For example, processing circuitry 50 may control sensing circuitry 52 to obtain a fourth electrogram vie a fourth vector including second pace/sense electrode 36B and a third pace/sense electrode (not illustrated in FIGS. 1 and 2) distal to defibrillation electrode 32B. In some examples, the fourth electrogram is proportional to a difference in electric potential between second pace/sense electrode 36B and the third pace/sense electrode. Additionally, processing circuitry 50 may control sensing circuitry 52 to obtain a fifth electrogram via a fifth vector including second pace/sense electrode 36B and a second uncoated portion (not illustrated) located on second defibrillation electrode 32B. In some examples, the fifth electrogram is proportional to a difference in electric potential between second pace/sense electrode 36B and the second uncoated portion. The fifth vector may form a third angle with the fourth vector. In other words, a line which passes through second pace/sense electrode 36B and the third pace/sense electrode may form the third angle with a line that passes through second pace/sense electrode 36B and the second uncoated portion. In some examples, the third angle is within a range from thirty degrees to sixty degrees. However, the third angle is not meant to be limited to such a range. In some cases, the third angle may be less than thirty degrees or greater than sixty degrees. Since cardiac depolarizations are directional in nature and follow a three-dimensional path through heart 18 of patient 8, it may be beneficial for the fifth vector to form an angle with the fourth vector such that IMD 12 obtains different angular perspectives of directional cardiac depolarizations according to the fourth vector and the fifth vector.

Additionally, processing circuitry 50 may control sensing circuitry 52 to obtain a sixth electrogram via a sixth vector including the third pace/sense electrode and the second uncoated portion of second defibrillation electrode 32B. In some examples, the sixth electrogram is proportional to a difference in electric potential between the third pace/sense electrode and the second uncoated portion. The sixth vector may form a fourth angle with the fourth vector. In other words, a line which passes through second pace/sense electrode 36B and the third pace/sense electrode may form the fourth angle with a line that passes through the third pace/sense electrode and the second uncoated portion. In some examples, the fourth angle is within a range from thirty degrees to sixty degrees. However, the fourth angle is not meant to be limited to such a range. In some cases, the fourth angle may be less than thirty degrees or greater than sixty degrees. It may be beneficial for the sixth vector to form an angle with the fourth vector such that IMD 12 may obtain another angular perspective of the directional cardiac depolarizations in addition to the perspectives provided by the fourth vector and the fifth vector. Additionally, the fifth vector and the sixth vector may form an angle (e.g., within a range from 30 to 120 degrees) such that the fourth vector, the fifth vector, and the sixth vector form a triangle between second pace/sense electrode 36B, the third pace/sense electrode, and the second uncoated portion.

Second pace/sense electrode 36B, the third pace/sense electrode, and the second uncoated portion may, in some cases, be proximate to atria of heart 18. In some cases, processing circuitry 50 may be configured to store the fourth electrogram, the fifth electrogram, and the sixth electrogram in storage device 60 as a part of collected data 64, where the fourth electrogram, the fifth electrogram, and the sixth electrogram are different.

Although the set of vectors including the first vector, the second vector, the third vector, the fourth vector, the fifth vector, and the sixth vector are described herein with respect to sensing cardiac depolarizations, IMD 12 may also deliver electric stimulation (e.g., pacing pulses) according to the set of vectors. For example, processing circuitry 50 may control signal generation circuitry 54 to deliver electrical stimulation according to any one or more of the first vector, the second vector, and the third vector in order to deliver electrical stimulation to ventricles of heart 18. Additionally, processing circuitry 50 may control signal generation circuitry 54 to deliver electric stimulation according to any one or more of the fourth vector, the fifth vector, and the sixth vector in order to deliver electric stimulation to the atria of heart 18. Since each of the set of vectors offer different perspectives with respect to heart 18, it may be beneficial for IMD 12 to selectively deliver electric stimulation according to a selected one or more of the set of vectors.

Power source 66 is configured to deliver operating power to the components of IMD 12. Power source 66 may include a battery and a power generation circuit to produce the operating power. In some examples, the battery is rechargeable to allow extended operation. In some examples, recharging is accomplished through proximal inductive interaction between an external charger and an inductive charging coil within IMD 12. Power source 66 may include any one or more of a plurality of different battery types, such as nickel cadmium batteries and lithium ion batteries.

Although six vectors are described with respect to FIG. 2, processing circuitry 50 may be configured to determine data corresponding to other vectors. Such other vectors may represent differences in measured parameters between any two or more of electrodes 20, 32A, 32B, 36A, and 36B. For example, although the six vectors are described herein as including two electrodes, one or more techniques of this disclosure may be implemented such that a vector may include three or more electrodes, where at least two of the three or more electrodes are connected as a common node. In this way, a vector may include two nodes, each node including one or more electrodes. Additionally, each of the six vectors described with respect to FIG. 2 may correspond to an opposite polarity vector. For example, IMD 12 may change the polarity of any of the six vectors to obtain data corresponding to the respective opposite polarity vector.

A clinician or another user may retrieve data from IMD 12 using external device 38, or by using another local or networked computing device (e.g., a remote computer located with the clinician) configured to communicate with processing circuitry 50 via communication circuitry 58. For example, a clinician may retrieve collected data 64 for analysis using external device 38. In some examples, the clinician may also program parameters of IMD 12 (e.g., therapy and sensing parameters 62 using external device 38 or another local or networked computing device.

Although processing circuitry 50 of IMD 12 is described above as being configured to control sensing circuitry 52 to sense cardiac electrogram signals and signal generation circuitry 54 to deliver cardiac pacing according to a selected one or more vectors from a set of vectors, any steps described herein as being carried out by processing circuitry 50 of IMD 12 may carried out by processing circuitry of one or more other devices. For example, processing circuitry of external device 38, a remote computer, or any other suitable implantable or external device or server, may be configured to carry out one or more of the steps of the techniques described herein, such as via communication circuitry 58 of IMD 12.

Figure 3:
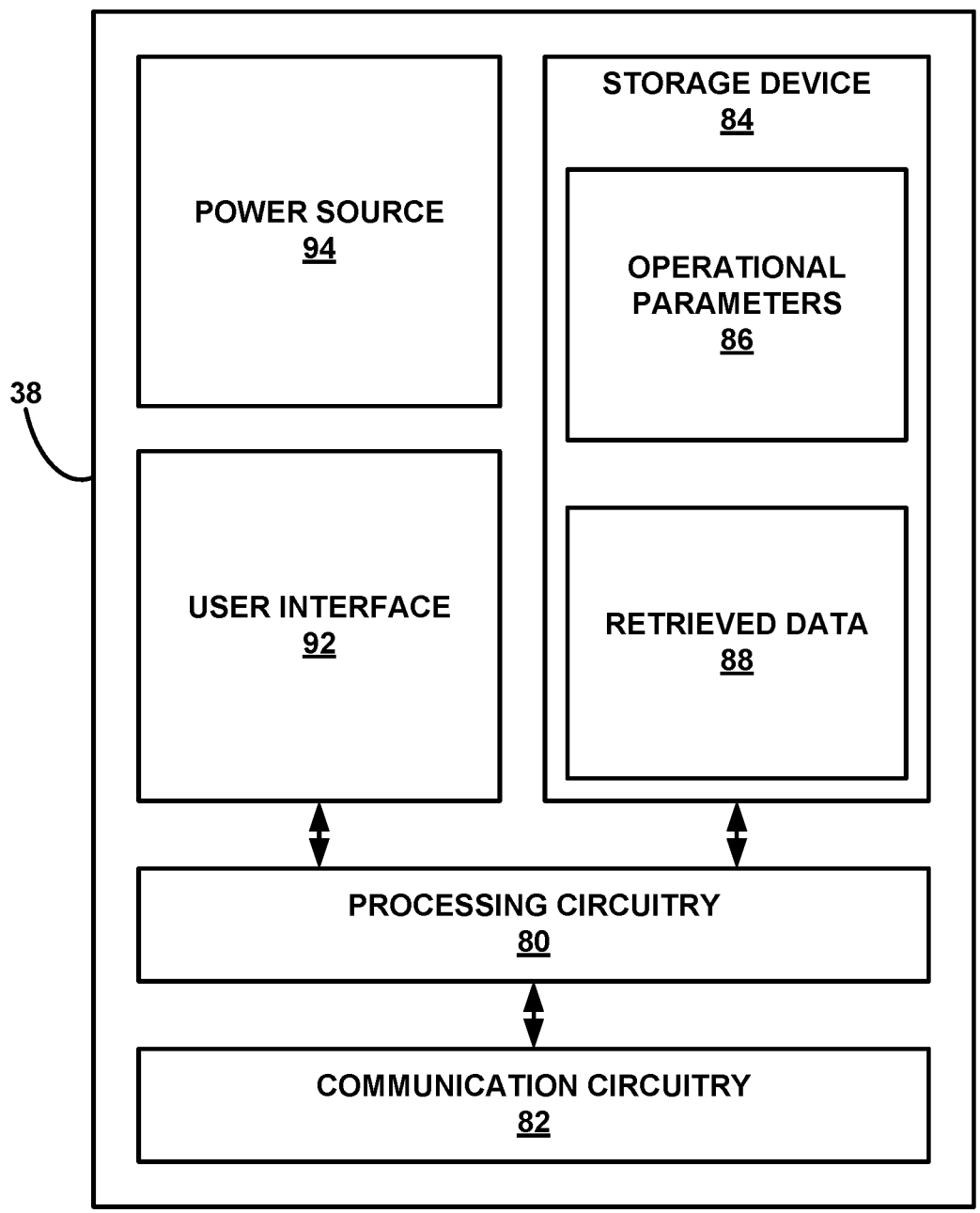
FIG. 3 is a block diagram illustrating an example configuration of components of the external device of FIG. 1A, in accordance with one or more techniques described herein.

FIG. 3 is a block diagram illustrating an example configuration of components of external device 38, in accordance with one or more techniques described herein. In the example of FIG. 3, external device 38 includes processing circuitry 80, communication circuitry 82, storage device 84, user interface 92, and power source 94. Storage device 84 is configured to store operational parameters 86 and retrieved data 88.

Processing circuitry 80, in one example, may include one or more processors that are configured to implement functionality and/or process instructions for execution within external device 38. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 12. Under the control of processing circuitry 80, communication circuitry 82 may receive downlink telemetry from, as well as send uplink telemetry to, IMD 12 or another device. In some examples, communication circuitry 82 includes a first set of communication circuitry configured for transmitting and receiving signals according to a communication protocol developed by the manufacturer of IMD 12 or a third-party developer. In some such examples, communication circuitry 82 further includes a second set of communication circuitry which defines a Bluetooth® radio configured for transmitting and receiving signals according to Bluetooth® communication protocols. However, communication circuitry 82 does not necessarily include separate sets of circuitry corresponding to different communication protocols. In some examples, communication circuitry 82 includes a single set of circuitry configured for transmitting and receiving signals according to a plurality of communication protocols.

In some examples, communication circuitry 82 includes any combination of a Bluetooth® radio, an electronic oscillator, frequency modulation circuitry, frequency demodulation circuitry, amplifier circuitry, and power switches such as a MOSFET, a BJT, an IGBT, a JFET, or another element that uses voltage for its control.

Storage device 84 may be configured to store information within external device 38 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 38 to temporarily store information during program execution.

Data exchanged between external device 38 and IMD 12 may include any of operational parameters 86 stored in storage device 84. External device 38 may transmit data including computer readable instructions which, when implemented by IMB 12, may control IMD 12 to change one or more operational parameters according to operational parameters 86 and/or export collected data. For example, processing circuitry 80 may transmit an instruction to IMB 12 which requests IMB 12 to export collected data (e.g., a portion of collected data 64) to external device 38. In turn, external device 38 may receive the collected data from IMB 12 and store the collected data in storage device 84 (e.g., as retrieved data 88). Additionally, or alternatively, processing circuitry 80 may export instructions to IMD 12 requesting IMD 12 to update electrode vectors for therapy or sensing according to operational parameters 86. For example, processing circuitry 80 may export instructions to IMD 12 requesting IMD 12 to update which vectors (e.g., the first vector, the second vector, the third vector, the fourth vector, the fifth vector, the sixth vector, or another vector) are used to monitor the electrical signals of heart 18.

A user, such as a clinician or patient 8, may interact with external device 38 through user interface 92. User interface 92 includes a display (not shown), such as an LCD or LED display or other type of screen, with which processing circuitry 80 may present information related to IMD 12 (e.g., EGM signals obtained using one of the set of vectors). In addition, user interface 92 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 38 and provide input. In other examples, user interface 92 also includes audio circuitry for providing audible notifications, instructions or other sounds to patient 8, receiving voice commands from patient 8, or both. Storage device 84 may include instructions for operating user interface 92 and for managing power source 94.

Power source 94 is configured to deliver operating power to the components of external device 38. Power source 94 may include a battery and a power generation circuit to produce the operating power. In some examples, the battery is rechargeable to allow extended operation. Recharging may be accomplished by electrically coupling power source 94 to a cradle or plug that is connected to an alternating current (AC) outlet. In addition, recharging may be accomplished through proximal inductive interaction between an external charger and an inductive charging coil within external device 38. In other examples, traditional batteries (e.g., nickel cadmium or lithium ion batteries) may be used. In addition, external device 38 may be directly coupled to an alternating current outlet to operate.

Figure 4A:
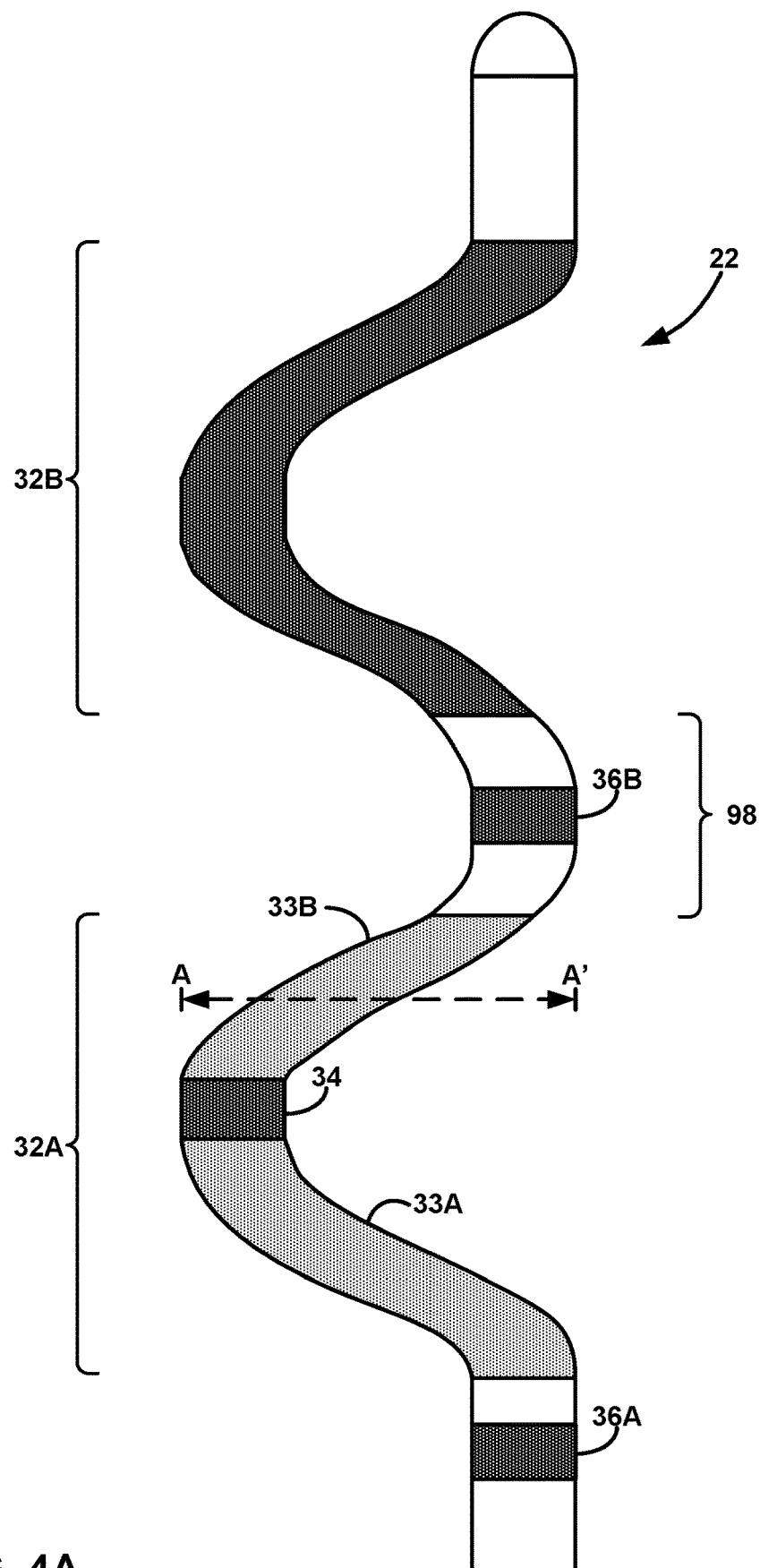
FIG. 4A is a front view of a distal portion of the medical lead of FIGS. 1A-1C, in accordance with one or more techniques described herein.

FIG. 4A is a front view of a distal portion of medical lead 22, in accordance with one or more techniques described herein. In the illustrated example, lead 22 includes first defibrillation electrode 32A, second defibrillation electrode 32B, first pace/sense electrode 36A, and second pace/sense electrode 36B. First defibrillation electrode 32A includes proximal coated portion 33A, distal coated portion 33B, and uncoated portion 34 between proximal coated portion 33A and distal coated portion 33B. In some examples, proximal coated portion 33A is a first proximal coated portion, distal coated portion 33B is a first distal coated portion, and uncoated portion 34 is a first uncoated portion. In some examples not illustrated in FIG. 4A, second defibrillation electrode 32B includes a second proximal coated portion, a second distal coated portion, and a second uncoated portion between the second proximal coated portion and the second distal coated portion.

Defibrillation electrodes 32, in some examples, are coil electrodes formed by a conductor. For example, first defibrillation electrode 32A and second defibrillation electrode 32B may represent coil electrodes disposed in-line with a wall of lead 22, around an exterior of the wall of lead 22, or within the wall of lead 22. Additionally, in some examples, defibrillation electrodes 32 may be flat ribbon electrode segments, paddle electrode segments, braided or woven electrode segments, mesh electrode segments, directional electrode segments, patch electrode segments or other types of electrode segments configured to deliver a defibrillation shock to the heart 18. Defibrillation electrodes 32 may be formed from any of a number of conductive material(s), including but not limited to, metals, metal oxides, metal alloys, coated metals and composite materials based on a combination of platinum, gold, iridium, titanium, tantalum, vanadium, aluminum, copper, zirconium, carbon, graphene, diamond, zirconium, diamond like coatings (DLC), silicon, and/or boron. This also includes glasses and dielectric materials such as borosilicate or chalcogenide glass, zirconia, alumina as well as conductive polymers, semiconductors and conductive ceramics in pure form or with additives such as boron, carbon, gold, silver and similar metal particles and/or fibers from micro to nano dimensions.

In some examples, an electrically insulating material covers respective conductors of defibrillation electrode 32A at coated portions 33. The electrically insulating material, in some cases, prevents conduction of relatively lower voltage signals (e.g., less than 100 Volts (V)) between coated portions 33 and tissue of patient 8. Additionally, the electrically insulating material may allow conduction of relatively higher voltage signals (e.g., greater than or equal to 100 V) between coated portions 33 and tissue of patient 8. For example, coated portions 33 may be configured to prevent transmission of a pacing pulse, prevent sensing of a cardiac depolarization, and allow transmission of a defibrillation shock, since a voltage of the defibrillation shock is substantially higher than the voltages of the cardiac depolarization and the pacing pulse. The electrically insulating material may be any of a number of materials, such as single or combinations of tantalum pentoxide, titanium oxides, zirconium oxide, vanadium oxide, niobium oxide, doped silicon, silicon dioxide, boron doped diamond, doped glass, ceramic coating or polymer composite or other material that has the property of substantially preventing the transmission or delivery of low voltages while not substantially preventing the transmission or delivery of high voltages.

In some examples, defibrillation electrode 32A is not coated with an electrically insulating material at uncoated portion 34. In other words, uncoated portion 34 may represent a section of exposed conductor material on defibrillation electrode 32A, such sections of exposed conductor material allowing for the transmission of lower-voltage signals. For example, uncoated portion 34 may be configured to both allow conduction of relatively lower voltage signals (e.g., less than 100 V) and allow conduction of relatively higher voltage signals (e.g., greater than or equal to 100V). For example, uncoated portion 34 may be configured to transmit a defibrillation shock, transmit a pacing pulse, sense an electrical signal corresponding to a cardiac depolarization, or any combination thereof. As such, an entire length of a defibrillation electrode such as defibrillation electrode 32A may be configured to conduct a defibrillation shock delivered by signal generation circuitry within housing 20, and a portion (e.g., uncoated portion 34) of defibrillation electrode 32A may be configured to transmit pacing pulses and sense cardiac depolarizations. In this way, uncoated portion 34 of defibrillation electrode 32A may perform at least some of the same functionalities as pace/sense electrodes 36.

The electrically insulating material may, in some examples, extend around the entire circumference of coated portions 33 of defibrillation electrodes 32. In other examples, the electrically insulating material may extend around a portion of the circumference of coated portions 33. For example, the electrically insulating material may extend around a portion of the circumference of coated portions 33 that is facing heart 18. The electrically insulating material may be any of a number of material such as single or combinations of tantalum pentoxide, titanium oxides, Zirconium oxide, Vanadium oxide, niobium oxide, doped silicon, silicon dioxide, boron doped diamond, doped glass, ceramic coating or polymer composite or other material that has the property of substantially preventing the transmission or delivery of low voltages while not substantially preventing the transmission or delivery of high voltages. A thickness of the electrically insulating material may vary based on a type of material that defibrillation electrode 32A is made of, the type of electrically insulating material, dimensions of the respective coated portion 33, an expected depth and position of the distal portion of lead 22, e.g., substernal or subcutaneous location. In examples where tantalum pentoxide is the electrically insulating material, the thickness of the electrically insulating material may be within a range from 0.2 micrometers ($\mu$m) to less than or equal to 2.0 $\mu$m. However, other thicknesses may be utilized without departing from the scope of this disclosure. In one example, coated portions 33 are coated with tantalum pentoxide having a thickness within a range from 0.6 $\mu$m to 0.9 $\mu$m microns. In such an example, the tantalum pentoxide coating significantly blocks current flow up to 100V, thus preventing the sensing of cardiac depolarization events and preventing the transmission of pacing pulses. Additionally, in such an example, electrical signals having voltages higher than 100V (e.g., defibrillation shocks) overcome the electrically insulating property of the tantalum pentoxide coating and may conduct through coated portions 33 of defibrillation electrodes 32.

A length of each of defibrillation electrodes 32 may be within a range between 2 cm and 16 cm. However, lengths of greater than 16 cm and less than 2 cm may be utilized without departing from the scope of this disclosure. In some examples, defibrillation electrode 32A and defibrillation electrode 32B are the same length. In other examples, defibrillation electrode 32A and defibrillation electrode 32B are of differing lengths. In some examples, first defibrillation electrode 32A and second defibrillation electrode 32B may be spaced apart on lead 22 by a distance within a range from 0.1 cm to 3 cm. In the example illustrated in FIG. 4A, first defibrillation electrode 32A and second defibrillation electrode 32B are spaced apart by enough of a distance such that second pace/sense electrode 36B is placed between first defibrillation electrode 32A and second defibrillation electrode 32B. In some examples, second pace/sense electrode 36B may be located at or near a median point along a section of lead 22 that separates first defibrillation electrode 32A and second defibrillation electrode 32B (i.e., lead section 98). For example, a center of second pace/sense electrode 36B may be located within a range between 35% of the length of lead section 98 from a proximal end of lead section 98 to 65% of the length of lead section 98 from the proximal end of lead section 98. In other words, in an example where a length of lead section 98 is 2 cm, the center of second pace/sense electrode 36B may be located within a range from 0.7 cm from the proximal end of first lead section 98 to 1.3 cm from the proximal end of lead section 98.

Coated portions 33 and uncoated portion 34 may vary in size. In some examples, an uncoated portion (e.g., uncoated portion 34) may be less than or equal to 25% of the length the respective defibrillation electrode 32A. Additionally, in some examples, uncoated portion 34 may be less than or equal to 10% of the length of the respective defibrillation electrode 32A. In some examples, a combined length and/or surface area of all of the uncoated portion 34 of defibrillation electrodes 32 may be less than or equal to 25% of a combined length and/or surface area of defibrillation electrodes 32 or less than or equal to 10% of the combined length and/or surface area of the defibrillation electrodes 32. Each of the uncoated portion 34 may, in some examples, have a surface area that is less than or equal to 100 square millimeters ($mm^2$). In other instances, uncoated portion 34 may have a surface area that is less than or equal to 10 $mm^2$. Uncoated and coated portions may have sizes other than those described above.

Uncoated portion 34 may be located at or near a median point along the length of first defibrillation electrode 32A. For example, a center of uncoated portion 34 may be located within a range between 35% of the length of first defibrillation electrode 32A from the proximal end of first defibrillation electrode 32A to 65% of the length of first defibrillation electrode 32A from the proximal end of first defibrillation electrode 32A. In other words, in an example where first defibrillation electrode 32A is 5 cm in length, the center of uncoated portion 34 may be located within a range from 1.75 cm from the proximal end of first defibrillation electrode 32A to 3.25 cm from the proximal end of first defibrillation electrode 32A. In this way, the respective coated portions (e.g., proximal coated portion 33A and distal coated portion 33B) may be the same length or differ in length based on the location of uncoated portion 34 along first defibrillation electrode 32A. For example, if uncoated portion 34 is located closer to the proximal end of first defibrillation electrode 32A than the distal end of first defibrillation electrode 32A, a length of proximal coated portion 33A may be shorter than a length of distal coated portion 33B. Additionally, if uncoated portion 34 is located closer to the distal end of first defibrillation electrode 32A than the proximal end of first defibrillation electrode 32A, a length of proximal coated portion 33A may be longer than a length of distal coated portion 33B.

Figure 4B:
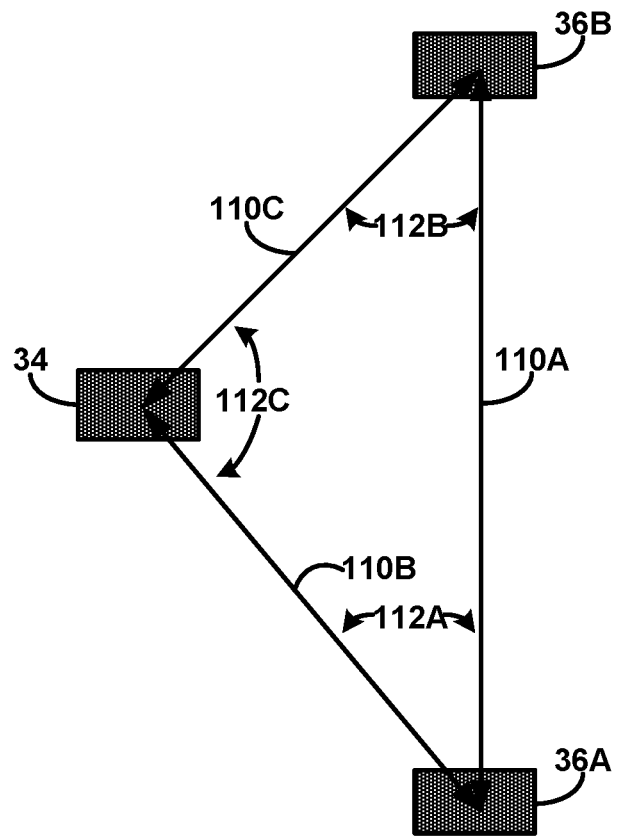
FIG. 4B is a conceptual diagram illustrating vectors available from the distal portion of the medical lead of FIG. 4A, in accordance with one or more techniques described herein.

FIG. 4B is a conceptual diagram illustrating vectors available from the distal portion of medical lead 22, in accordance with one or more techniques described herein. The example illustrated in FIG. 4B includes uncoated portion 34A of defibrillation electrode 32A, first pace/sense electrode 36A, and second pace/sense electrode 36B. Additionally, FIG. 4B illustrates first vector 110A, second vector 110B, third vector 110C (collectively, "vectors 110") and angles 112A-112C (collectively, "angles 112").

In some examples, IMD 12 may be configured to sense, via electrodes on the distal portion of lead 22, cardiac electrograms, e.g., including cardiac depolarizations, or other electrical signals according vectors 110. Each vector of vectors 110 may, in some cases, represent a difference in electric potential between respective electric potential signals obtained by a pair of electrodes (e.g., any combination of uncoated portion 34 of defibrillation electrodes 32, pace/sense electrodes 36, and electrodes disposed on housing 20 of IMD 12). In some examples, a vector may be defined by a set of parameters including a combination of two or more electrodes, a spatial arrangement of the two or more electrodes, and a polarity of each electrode of the two or more electrodes.

For example, processing circuitry 50 may be configured to control sensing circuitry 52 to obtain a first electrogram via first vector 110A which includes first pace/sense electrode 36A and second pace/sense electrode 36B. In some examples, the first electrogram is proportional to a difference in electric potential between first pace/sense electrode 36A and second pace/sense electrode 36B. Additionally, processing circuitry 50 may control sensing circuitry 52 to obtain a second electrogram via second vector 110B including first pace/sense electrode 36A and uncoated portion 34 of first defibrillation electrode 32A. In some examples, the second electrogram is proportional to a difference in electric potential between first pace/sense electrode 36A and uncoated portion 34. Second vector 110B may form angle 112A with first vector 110A. In some examples, angle 112A is within a range from 30 degrees to 60 degrees. In one example, angle 112A is 45 degrees. Since cardiac depolarizations are directional in nature and follow a three-dimensional path through heart 18 of patient 8, it may be beneficial for first vector 110A to form an angle with the second vector 110B such IMD 12 may obtain different angular perspectives of a directional cardiac depolarization.

Additionally, processing circuitry 50 may control sensing circuitry 52 to obtain a third electrogram via third vector 110C including second pace/sense electrode 36B and uncoated portion 34 of first defibrillation electrode 32A. In some examples, the third electrogram is proportional to a difference in electric potential between second pace/sense electrode 36B and uncoated portion 34. Third vector 110C may form angle 112B with first vector 110A. In some examples, the angle 112B is within a range from 30 degrees to 60 degrees. For example, angle 112B may be 45 degrees. It may be beneficial for third vector 110C to form an angle with first vector 110A such that IMD 12 may obtain another angular perspective of the directional cardiac depolarization in addition to the perspectives provided by first vector 110A and second vector 110B. Additionally, second vector 110B and third vector 110C may form angle 112C such that first vector 110A, second vector 110B, and third vector 110C form a triangle between first pace/sense electrode 36A, second pace/sense electrode 36B, and uncoated portion 34.

In some examples, angle 112C is within a range from 60 degrees to 120 degrees. For example, angle 112C may be 90 degrees. Since first vector 110A, second vector 110B, and third vector 110C form a triangle, a summation of angle 112A, angle 112B, and angle 112C may be 180 degrees.

First pace/sense electrode 36A, second pace/sense electrode 36B, and uncoated portion 34 may, in some cases, be proximate to a ventricle of heart 18. In some cases, IMD 12 may store the first electrogram, the second electrogram, and the third electrogram in a storage device (e.g., storage device 60).

Although the set of vectors including vectors 110 are described herein with respect to sensing cardiac depolarizations, IMD 12 may also deliver electric stimulation (e.g., pacing pulses) according to vectors 110. For example, processing circuitry 50 may control signal generation circuitry 54 to deliver electrical stimulation according to any one or more of first vector 110A, second vector 110B, and third vector 110C in order to deliver electrical stimulation to ventricles of heart 18. Since each of the set of vectors offer different perspectives with respect to heart 18, it may be beneficial for IMD 12 to deliver electric stimulation according to different combinations of the set of vectors.

Since lead 22 is implanted within patient 8, and patient 8 moves about over the course of time, lead 22 may migrate relative to heart 18 after lead 22 is implanted within patient 8. Angles 112, in some cases, may change over a period of time due to such migration. For example, if the distal portion of lead 22 is compressed such that pace/sense electrodes 36 move closer together, angles 112A and 112B, may increase while angle 112C and decreases. Additionally, if the distal portion of lead 22 is stretched such that pace/sense electrodes 36 move farther apart, angles 112A and 112B may decrease while angles 112C increases. Any sort of relative movement of uncoated portion 34 and pace/sense electrodes 36 may cause angles 112 to change. Although three vectors 110 are described with respect to FIG. 4B, IMD 12 may be configured to collect data or deliver therapy (e.g., pacing pulses) according to other vectors not illustrated in FIG. 4B. Such other vectors may represent differences in measured parameters between any two or more of uncoated portion 34 of defibrillation electrodes 32, pace/sense electrodes 36, and electrodes disposed on can 20 of IMD 12.

Figure 5A:
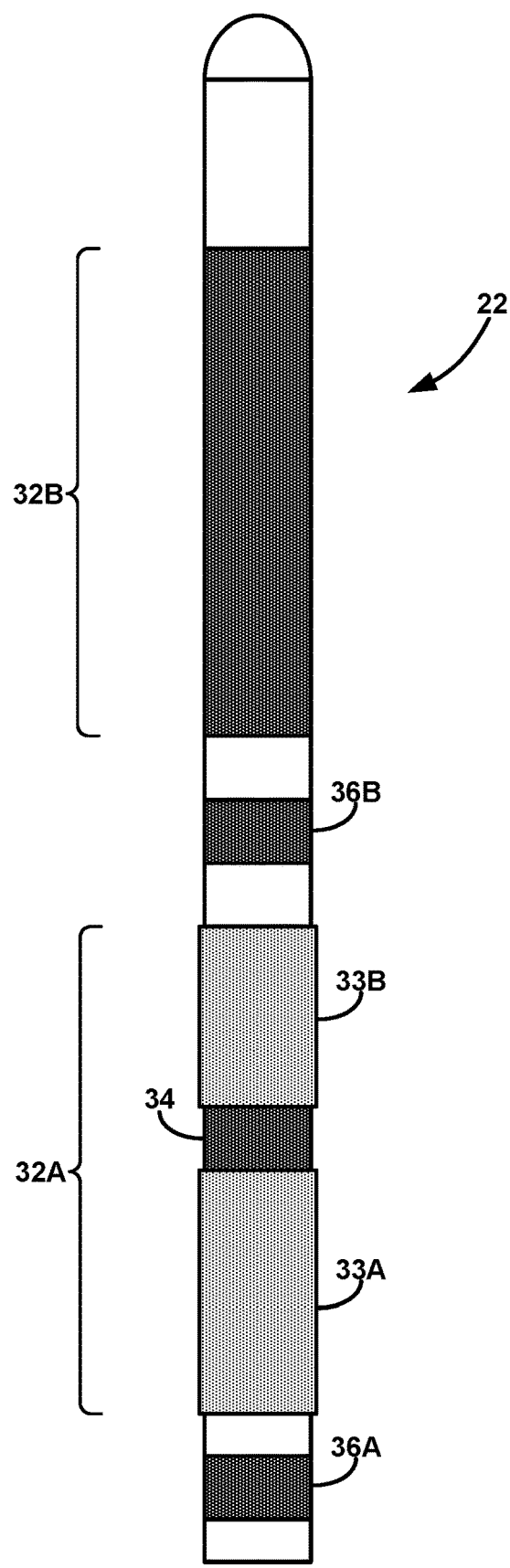
FIG. 5A is a side view of the distal portion of the medical lead of FIG. 4A, in accordance with one or more techniques described herein.

FIG. 5A is a side view of the distal portion of medical lead 22, in accordance with one or more techniques described herein. Although the distal portion of medical lead 22 forms a curvilinear shape, from a side view, the distal portion of medical lead 22 appears to be straight. For example, the curvilinear portions of the distal portion of medical lead 22 extend into and out from the plane of FIG. 5A. In other words, FIG. 5A illustrates a view of lead 22 where the line extending from A to A' as seen in FIG. 4A extends into the page. As such, defibrillation electrodes 32 having coated portions 33 and uncoated portion 34, and pace/sense electrodes 36, may be represented in FIG. 5A according to the side view of the distal end of lead 22.

Figure 5B:
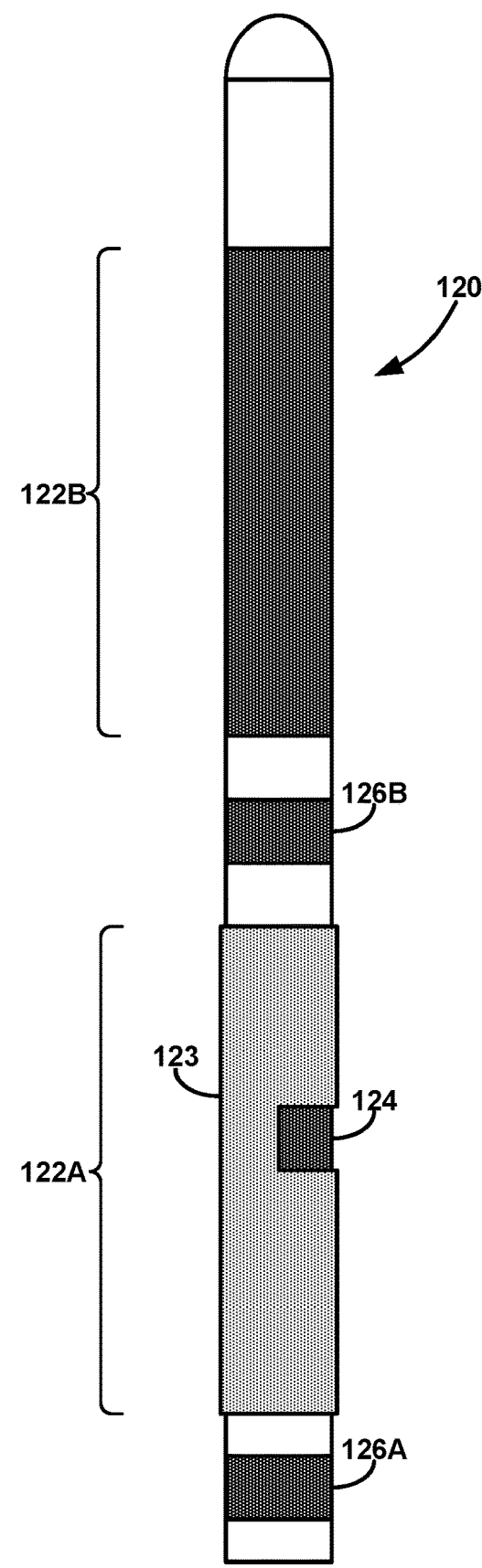
FIG. 5B is a side view of a distal portion of another example medical lead, in accordance with one or more techniques described herein.

FIG. 5B is a side view of a distal portion of another example medical lead 120, in accordance with one or more techniques described herein. Medical lead 120 may be similar to medical lead 22 except for differences outlined below. The example of FIG. 5B may include first defibrillation electrode 122A and second defibrillation electrode 122B (collectively, "defibrillation electrodes 122"), and pace/sense electrode 126A and pace/sense electrode 126B (collectively, "pace/sense electrodes 126"). Defibrillation electrode 122A includes coated portion 123 and uncoated portion 124. Second defibrillation electrode 122B may, in some cases, be entirely uncoated. The example of FIG. 5B may be substantially the same as the example of FIGS. 4A, 4B, and 5A except that in the example of FIG. 5B, uncoated portion 124 may be partially disposed around the circumference of lead 22 rather than being fully disposed around the circumference of lead 22. The remaining portions of the circumference of lead 22 (e.g., the portion that does not include uncoated portions 124) may be coated by the electrically insulating material. As such, coated portion 123 may cover portions of the respective defibrillation electrodes 122 proximal and distal to uncoated portion 124 and the remaining portions of the circumference of lead 22 that do not include uncoated portion 124.

Figure 6:
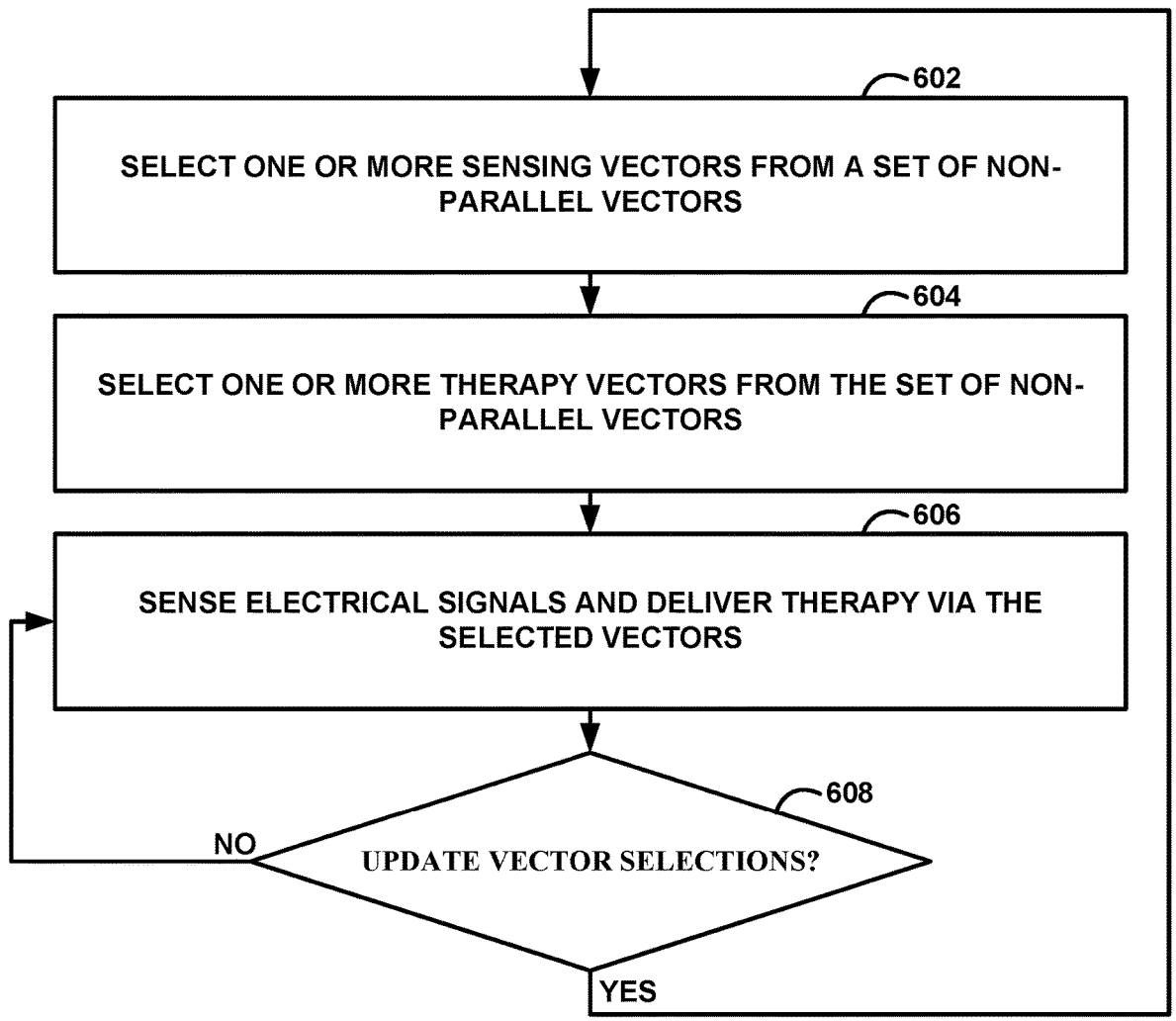
FIG. 6 is a flow diagram illustrating an example operation for sensing electrical signals, in accordance with one or more techniques of this disclosure.

FIG. 6 is a flow diagram illustrating an example operation for sensing electrical signals, in accordance with one or more techniques of this disclosure. For convenience, FIG. 6 is described with respect to IMD 12 and external device 38 of FIGS. 1-5. However, the techniques of FIG. 6 may be performed by different components of IMD 10 or by additional or alternative medical devices.

IMD 12, in some examples, may include lead 22. Lead 22 may include a lead body having a curvilinear shape. For example, a distal portion of lead 22 may include one or more arc-shaped portions. The distal portion of lead 22 may include two arc-shaped portions, which together may resemble the Greek letter epsilon, "ε." In some examples, defibrillation electrodes 32 are each carried by one of the two respective arc-shaped portions of the lead body distal portion. The two arc-shaped portions extend or curve in the same direction away from a central axis of the distal portion of lead 22. In some examples, pace/sense electrodes 36 may be disposed on the lead body such that pace/sense electrodes 36 are substantially aligned with the central axis. In such examples, mid-points of defibrillation electrodes 32 are laterally offset from pace/sense electrodes 36. Respective uncoated portion 34 of defibrillation electrodes 32 may be located at or near mid-points of defibrillation electrodes 32. Other examples of extra-cardiovascular leads including one or more defibrillation electrodes 32 and one or more pace/sense electrodes 36 carried by the curvilinear (e.g., curving, serpentine, undulating or zig-zagging) distal portion of lead 22 also may be implemented using the techniques described herein.

Processing circuitry 50 of IMD 12 selects one or more sensing vectors from a set of non-parallel vectors (602). Additionally, processing circuitry 50 selects one or more therapy vectors from the set of non-parallel vectors (604). The set of non-parallel vectors may include a first vector, a second vector, and a third vector. In some examples, the first vector may include first pace/sense electrode 36A and second pace/sense electrode 36B, the second vector may include first pace/sense electrode 36A and uncoated portion 34, and the third vector may include second pace/sense electrode 36B and uncoated portion 34. IMD 12 senses electrical signals and delivers therapy via the selected vectors (606). For example, sensing circuitry 52 of IMD 12 may sense the electrical signals according to the one or more selected sensing vectors and signal generation circuitry 54 of IMD 12 may deliver the therapy according to the one or more selected therapy vectors.

At block 608, processing circuitry 50 may determine whether to update the vector selections. For example, processing circuitry 50 may determine whether to update the vector selections based on one or more of a vector update schedule, user input, a detection of a loss of therapy effectiveness (e.g., a loss of therapy capture), and a detection of a loss of sensing effectiveness (e.g., a detection of under sensing of cardiac depolarizations). If processing circuitry 50 determines not to update the vector selections ("NO" branch of block 608), the example operation returns to block 606 and IMD 12 senses electrical signals and delivers therapy via the selected vectors. If processing circuitry 50 determines to update the vector selections ("YES" branch of block 608), the example operation returns to block 602 and processing circuitry 50 selects one or more sensing vectors from the set of non-parallel vectors and processing circuitry 50 selects one or more therapy vectors from the set of non-parallel vectors.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMB, an external programmer, a combination of an IMB and external programmer, an integrated circuit (IC) or a set of ICs, and/or discrete electrical circuitry, residing in an IMD and/or external programmer.

What is claimed is:

1. A medical device system comprising:
   a lead body;
   a high voltage electrode positioned on the lead body, the high voltage electrode comprising a proximal coated portion, a distal coated portion, and an uncoated portion between the proximal coated portion and the distal coated portion; and
   a set of low voltage electrodes positioned on the lead body, the set of low voltage electrodes comprising a first low voltage electrode and a second low voltage electrode distal to the first low voltage electrode; and
   sensing circuitry configured to:
   sense a first electrogram according to a first vector including the first low voltage electrode and the second low voltage electrode, wherein the first electrogram provides a first angular perspective of a directional cardiac depolarization of a heart of a patient; and
   sense a second electrogram according to a second vector including one of the first low voltage electrode or the second low voltage electrode and the uncoated portion, wherein the second electrogram provides a second angular perspective of the directional cardiac depolarization of the heart of the patient,
   wherein the first angular perspective of the directional cardiac depolarization is different than the second angular perspective of the directional cardiac depolarization, wherein an angle between the first vector and the second vector is within a range from thirty degrees to sixty degrees, causing the first angular perspective to be different than the second angular perspective.

2. The medical device system of claim 1, wherein the sensing circuitry is configured to:
   sense the second electrogram according to the second vector including the first low voltage electrode and the uncoated portion; and
   sense a third electrogram according to a third vector including the second low voltage electrode and the uncoated portion, wherein the third electrogram provides a third angular perspective of the directional cardiac depolarization of the heart of the patient.

3. The medical device system of claim 2, sensing circuitry is configured to at least one of:
   deliver, via the first low voltage electrode and the second low voltage electrode, one or more pacing pulses according to the first vector;
   deliver, via the first low voltage electrode and the uncoated portion, one or more pacing pulses according to the second vector; or
   deliver, via the second low voltage electrode and the uncoated portion, one or more pacing pulses according to the third vector.

4. The medical device system of claim 1, wherein the proximal coated portion and the distal coated portion are configured to prevent transmission of a pacing pulse and configured to allow transmission of a defibrillation shock, and
   wherein the uncoated portion is configured to at least one of transmit a defibrillation shock, transmit a pacing pulse, and sense an electrical signal corresponding to a cardiac depolarization.

5. The medical device system of claim 1, wherein the proximal coated portion and the distal coated portion are coated with an electrically insulating material configured to prevent conduction of signals having a first range of voltages between the high voltage electrode and patient tissue and allow conduction of signals having a second range of voltages between the high voltage electrode and the patient tissue, wherein the first range of voltages is lower than the second range of voltages.

6. The medical device system of claim 1, wherein the electrically insulating material is tantalum pentoxide.

7. The medical device system of claim 1,
   wherein the first low voltage electrode and the second low voltage electrode are aligned with a central axis of a distal portion of the lead body,
   wherein the uncoated portion is laterally offset from the central axis of the distal portion of the lead body,
   wherein the set of low voltage electrodes and the uncoated portion are positioned on the lead body such that an angle is formed between a first line passing through first low voltage electrode and the second low voltage electrode and a second line passing through one of the first low voltage electrode or the second low voltage electrode and the uncoated portion, wherein the first line corresponds to the central axis of the distal portion of the lead body, and wherein the angle between the first line and the second line corresponds to the angle between the first vector and the second vector.

8. The medical device system of claim 7, wherein the angle represents a first angle, wherein the first angle is formed between the first line and the second line passing through the first low voltage electrode and the uncoated portion, wherein the set of low voltage electrodes and the uncoated portion are positioned on the lead body such that a second angle is formed between the first line and a third line passing through the second low voltage electrode and the uncoated portion, and wherein the second angle is within a range from thirty degrees to sixty degrees.

9. The medical device system of claim 1, wherein the distal coated portion is distal to the uncoated portion, wherein the proximal coated portion is proximal to the uncoated portion, wherein the first low voltage electrode is proximal to the proximal coated portion, and wherein the second low voltage electrode is distal to the distal coated portion.

10. The medical device system of claim 1, wherein the lead body comprises a curvilinear portion, wherein the high voltage electrode is positioned on the curvilinear portion such that the high voltage electrode forms an arc, and wherein the uncoated portion is located at a peak of the arc.

11. The medical device system of claim 10, wherein the first low voltage electrode is proximal to the arc, and wherein the second low voltage electrode is distal to the arc.

12. The medical device system of claim 1, further comprising:

a first electrical conductor disposed within the lead body, wherein a distal end of the first electrical conductor is connected to the high voltage electrode and a proximal end of the first electrical conductor is connected to the sensing circuitry;

a second electrical conductor disposed within the lead body, wherein a distal end of the second electrical conductor is connected to the first low voltage electrode and a proximal end of the second electrical conductor is connected to the sensing circuitry; and a third electrical conductor disposed within the lead body, wherein a distal end of the third electrical conductor is connected to the second low voltage electrode and a proximal end of the third electrical conductor is connected to the sensing circuitry.

13. The medical device system of claim 1, wherein the uncoated portion is partially disposed around a circumference of the lead body, the remaining portion of the circumference of the lead body being coated with the electrically insulating material.

14. The medical device system of claim 1, wherein the high voltage electrode is a first high voltage electrode, the medical electrical lead further comprising:

a second high voltage electrode positioned on the lead body distal to the first high voltage electrode.

15. The medical device system of claim 14, wherein the second high voltage electrode is not coated by the electrically insulating material.

16. The medical device system of claim 14, wherein the proximal coated portion is a first proximal coated portion, wherein the distal coated portion is a first distal coated portion, wherein the uncoated portion is a first uncoated portion, wherein the second high voltage electrode comprises a second proximal coated portion, a second distal coated portion, and a second uncoated portion between the second proximal coated portion and the second distal coated portion, wherein the set of low voltage electrodes further comprises a third low voltage electrode distal to the second low voltage electrode, and wherein the sensing circuitry is further configured to:
sense a third electrogram according to a third vector including the second low voltage electrode and the third low voltage electrode, wherein the third electrogram provides a third angular perspective of the directional cardiac depolarization of the heart of a patient; and sense a fourth electrogram according to a fourth vector including one of the second low voltage electrode or the third low voltage electrode and the second uncoated portion, wherein the fourth electrogram provides a fourth angular perspective of the directional cardiac depolarization of the heart of the patient, wherein the third angular perspective of the directional cardiac depolarization is different than the fourth angular perspective of the directional cardiac depolarization.

17. The medical device system of claim 1, further comprising an implantable medical device (IMD) comprising the sensing circuitry.

18. The medical device system of claim 17, wherein the IMD is configured to be implanted subcutaneously or submuscularly.

19. The medical device system of claim 1, wherein a distal portion of the lead body is configured to be implanted within the patient superior or posterior to a sternum of the patient.

20. A method comprising:

sensing, by sensing circuitry, a first electrogram according to a first vector including a first low voltage electrode and a second low voltage electrode, wherein the first electrogram provides a first angular perspective of a directional cardiac depolarization of a heart of a patient, wherein a medical electrical lead comprises:
a lead body;
a high voltage electrode positioned on the lead body, the high voltage electrode comprising a proximal coated portion, a distal coated portion, and an uncoated portion between the proximal coated portion and the distal coated portion; and a set of low voltage electrodes positioned on the lead body, the set of low voltage electrodes comprising the first low voltage electrode and the second low voltage electrode distal to the first low voltage electrode; and sensing a second electrogram according to a second vector including one of the first low voltage electrode or the second low voltage electrode and the uncoated portion, wherein the second electrogram provides a second angular perspective of the directional cardiac depolarization of the heart of the patient, wherein the first angular perspective of the directional cardiac depolarization is different than the second angular perspective of the directional cardiac depolarization, wherein an angle between the first vector and the second vector is within a range from thirty degrees to sixty degrees, causing the first angular perspective to be different than the second angular perspective.

* * * * *